(12) United States Patent
Itou et al.

(10) Patent No.: US 7,494,478 B2
(45) Date of Patent: Feb. 24, 2009

(54) CATHETER ASSEMBLY

(75) Inventors: Takenari Itou, Fujinomiya (JP); Tetsuya Fukuoka, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 52 days.

(21) Appl. No.: 10/858,291

(22) Filed: Jun. 2, 2004

(65) Prior Publication Data

US 2005/0015007 A1 Jan. 20, 2005

(30) Foreign Application Priority Data

Jun. 2, 2003 (JP) ............................. 2003-157379

(51) Int. Cl.
*A61M 37/00* (2006.01)
*A61M 5/178* (2006.01)
*A61M 25/00* (2006.01)
*A61M 5/32* (2006.01)

(52) U.S. Cl. ................. 604/95.04; 604/95.03; 604/264; 604/272; 604/523; 604/532; 604/164.01

(58) Field of Classification Search ................. 604/158, 604/93.01, 95.03, 95.04, 263, 264, 271, 272, 604/523–525, 530, 532–533, 164, 164.13, 604/95.01
See application file for complete search history.

(56) References Cited

U.S. PATENT DOCUMENTS 4,563,181 A * 1/1986 Wijayarathna et al. ...... 604/523
4,636,346 A * 1/1987 Gold et al. .................. 264/139
4,909,787 A * 3/1990 Danforth .................. 604/95.03
4,983,169 A * 1/1991 Furukawa ............... 604/164.13
5,267,982 A * 12/1993 Sylvanowicz ............... 604/532
6,652,692 B2 * 11/2003 Pedersen et al. ............. 156/143
6,837,890 B1 * 1/2005 Chludzinski et al. ......... 606/108
2001/0005783 A1 * 6/2001 Hassett ....................... 604/523
2002/0188278 A1 * 12/2002 Tockman et al. ............. 604/527
2004/0019359 A1 * 1/2004 Worley et al. ............... 606/129

FOREIGN PATENT DOCUMENTS

| JP | 09-285546 | 11/1997 |
|---|---|---|
| WO | WO 97/13542 | 4/1997 |
| WO | WO 9713542 A1 * | 4/1997 |

* cited by examiner

*Primary Examiner*—Nicholas D Lucchesi
*Assistant Examiner*—Quynh-Nhu H Vu
(74) *Attorney, Agent, or Firm*—Buchanan Ingersoll & Rooney PC

(57) ABSTRACT

A catheter assembly comprises an outer catheter comprising a distal end curved portion having a first curved shape, and an inner catheter which comprises a distal end curved portion having a second curved shape different from the first curved shape and which can be inserted into the outer catheter so that the distal end curved portion thereof is located in the distal end curved portion of the outer catheter and be withdrawn therefrom. The distal end curved portion of the outer catheter is more flexible than the distal end curved portion of the inner catheter. A distal end portion of the catheter assembly, when the inner catheter is inserted in the outer catheter so that the distal end curved portion of the inner catheter is located in the distal end curved portion of the outer catheter, assumes a curved shape different from the first curved shape.

20 Claims, 17 Drawing Sheets

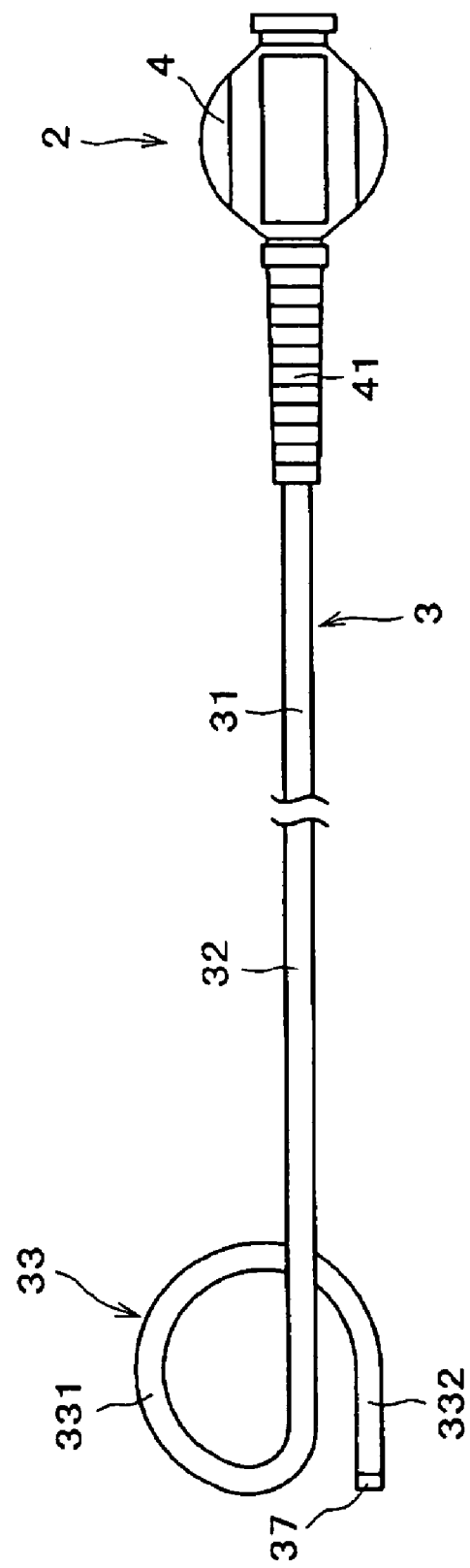

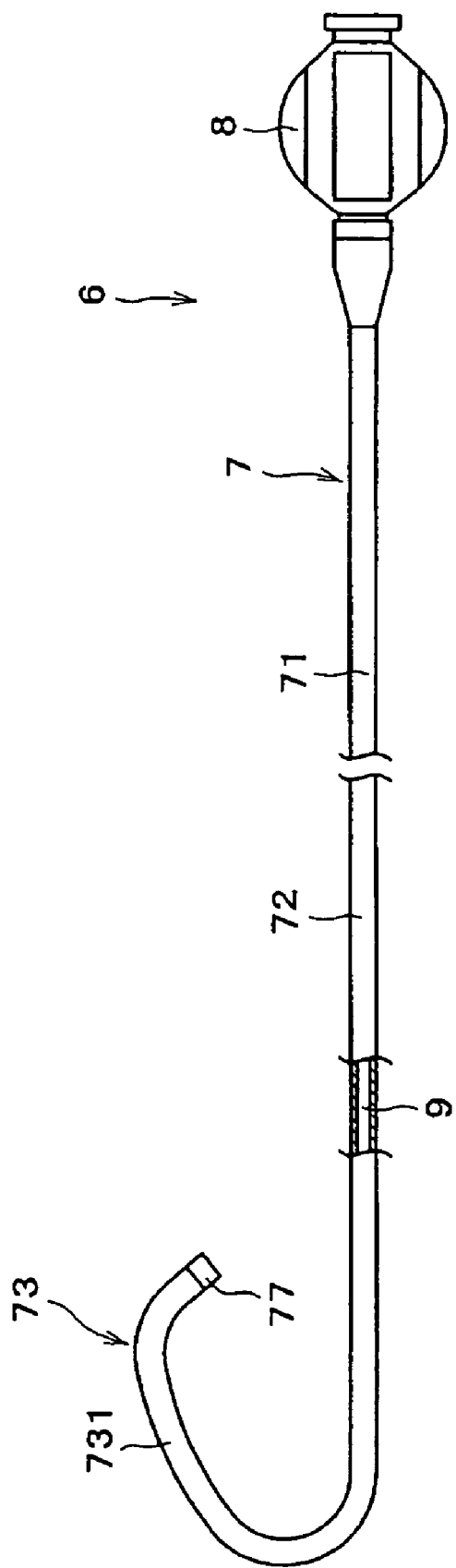

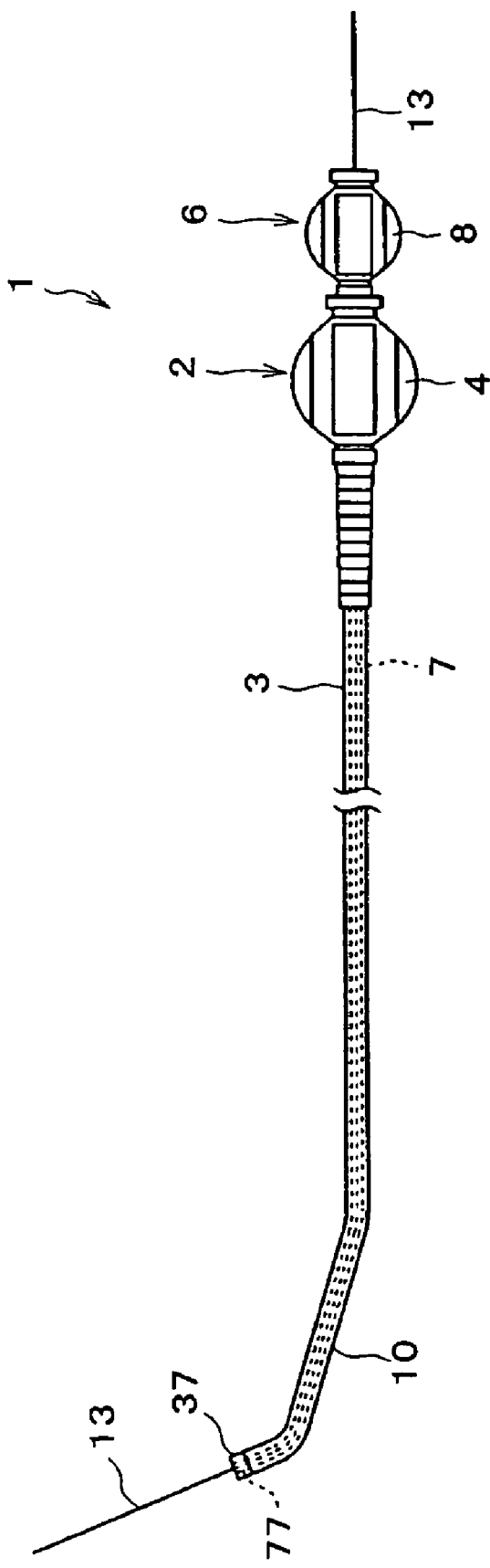

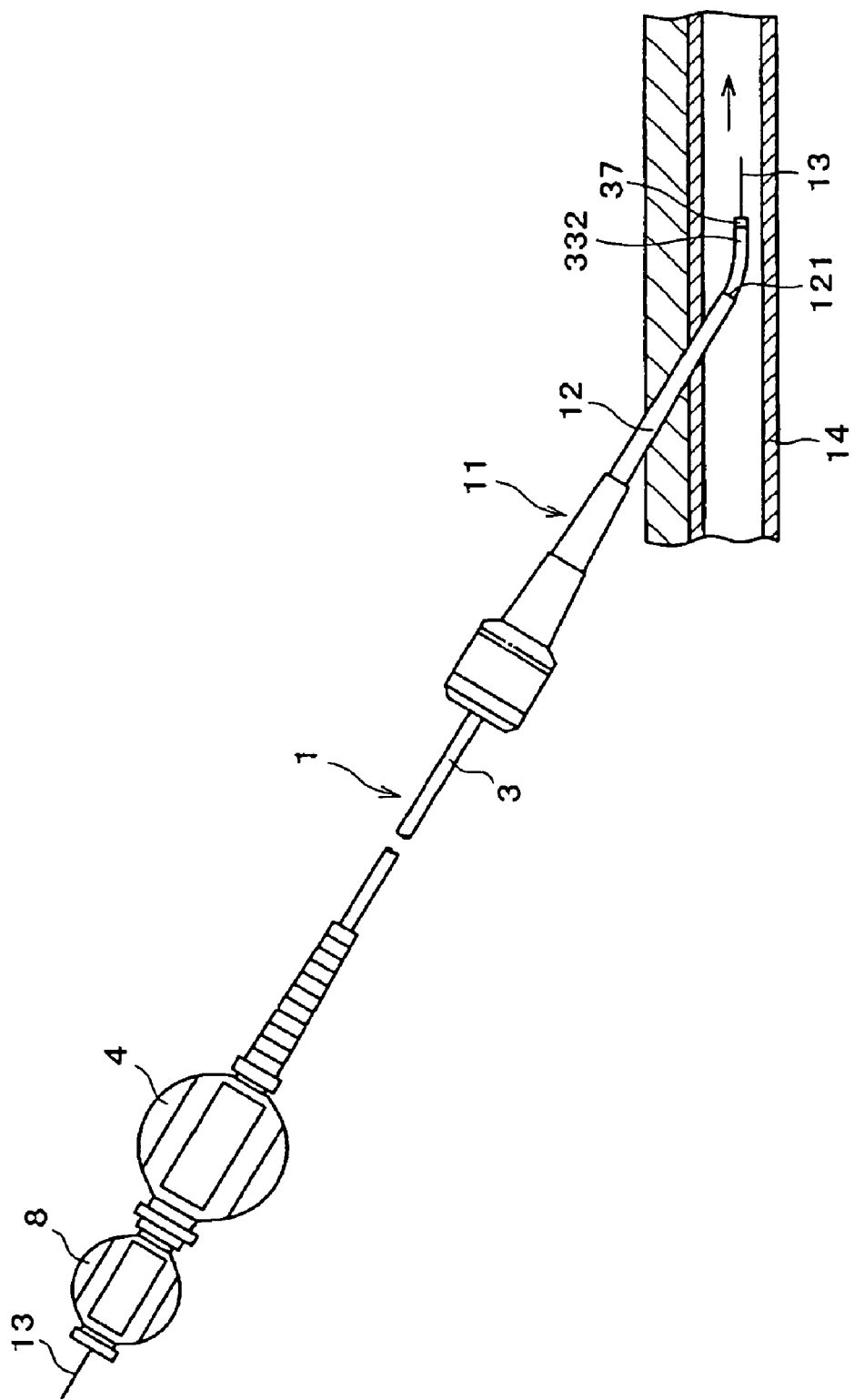

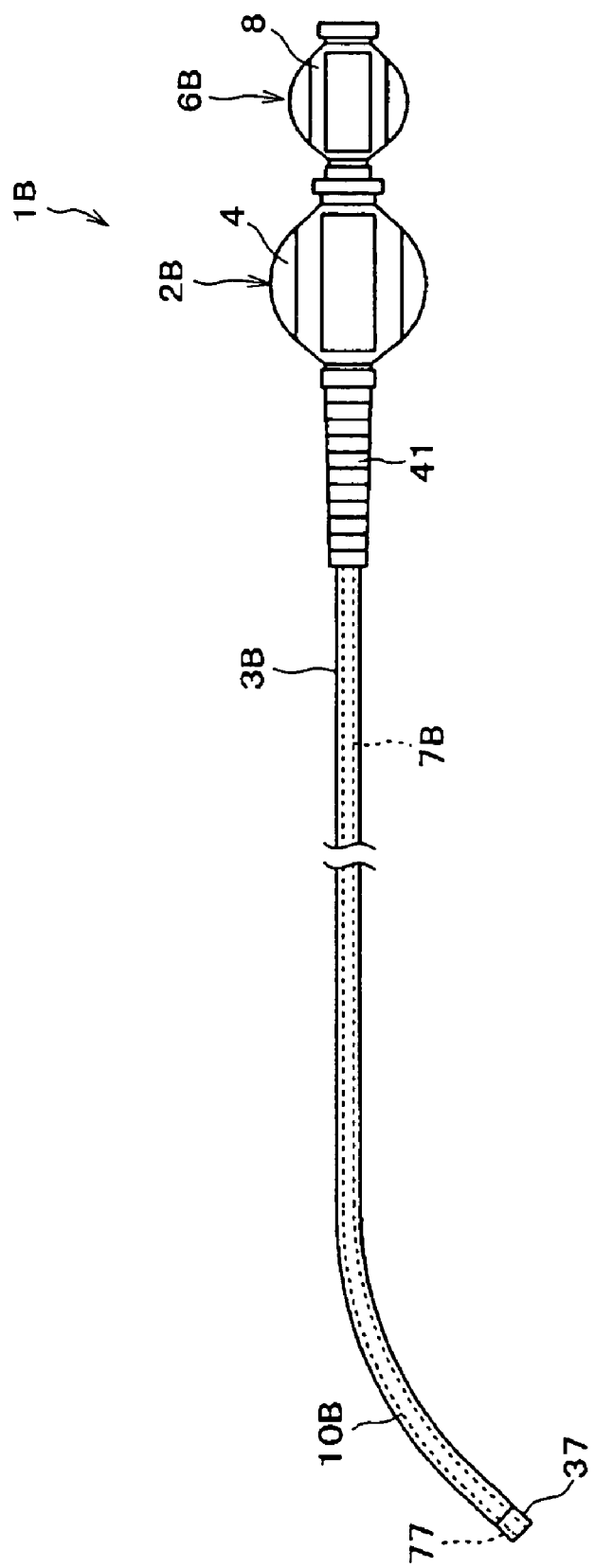

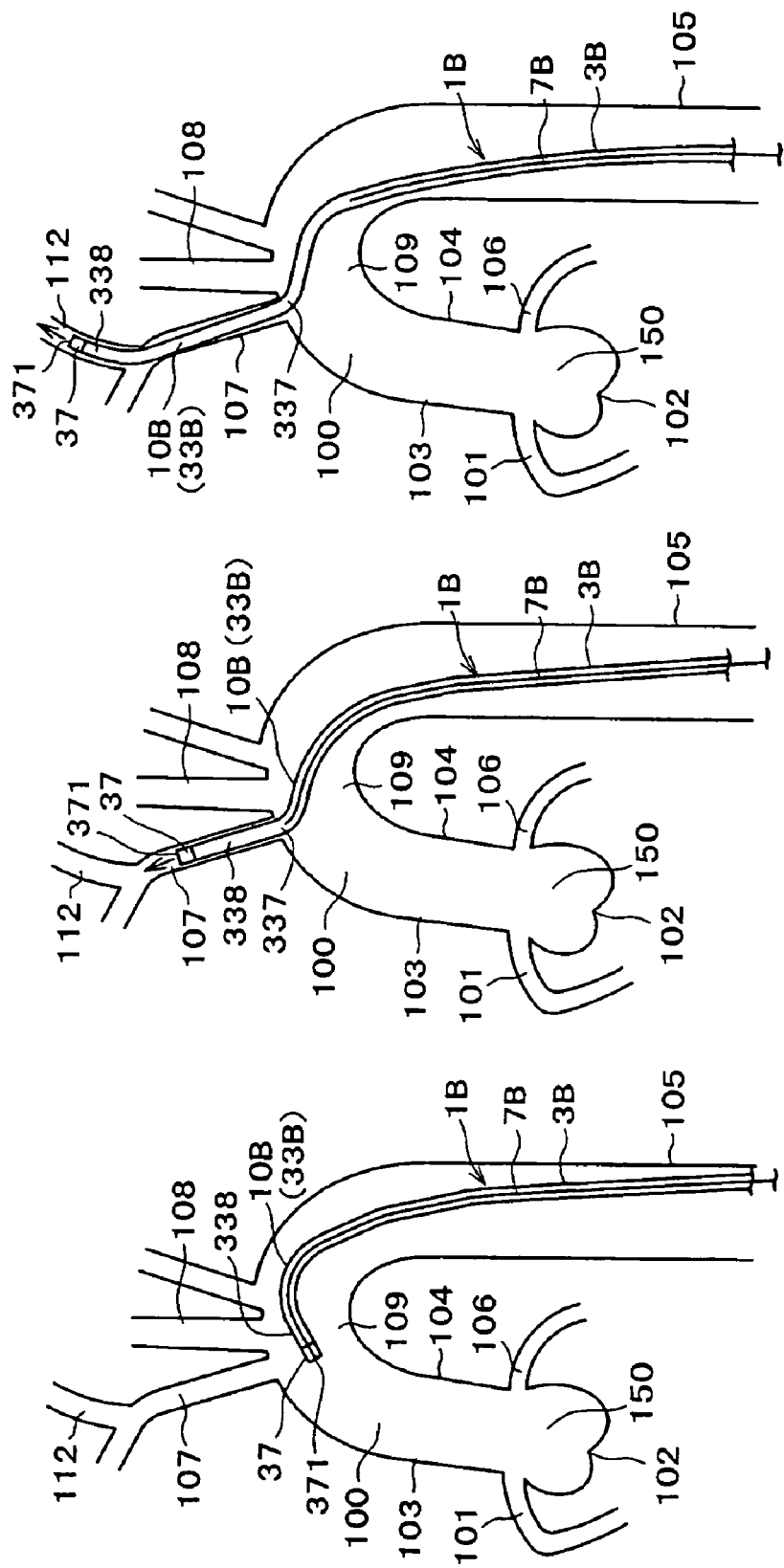

CATHETER ASSEMBLY

BACKGROUND OF THE INVENTION

The present invention relates to a catheter assembly which is used by being inserted into a heart or a peripheral tissue thereof, particularly, a left or right coronary artery (hereinafter also referred to simply as "the coronary artery"). More specifically, the present invention relates to a guiding catheter for guiding a procedure catheter such as a dilation catheter for PTCA, a stent delivery catheter, etc. to a target site of a blood vessel, or an angiography catheter for injecting a contrast medium to a target site of a blood vessel.

In selective angiography, for example, in the case of obtaining an angiographic image of the right coronary artery, it has been a common practice to insert the distal end of a catheter into the inlet of the right coronary artery, to inject a contrast medium through the catheter, and to obtain a selective angiographic image, for diagnosing the disease of the coronary artery. In such a case, a catheter assuming such a distal end shape as to permit easy insertion of the catheter into the right coronary artery is selected and used. Examples of the catheters designed by paying attention to the differences in the distal end shape include the Judkins type and the Anplatz type. Even in a specified one of these types, for example, in the Judkins type catheters, the catheter for the right coronary artery and the catheter for the left coronary artery differ from each other in the distal end shape.

Thus, different catheters must be selectively and appropriately used according to the difference in the target site (angiography site), namely, the difference between the right coronary artery and the left coronary artery. In addition, in the case of a patient having a blood vessel assuming a special anatomical shape, a further different catheter for exclusive use must be used.

Therefore, a great variety of catheters must be prepared in advance. Particularly in the case of angiography of both the right coronary artery and the left coronary artery, it is necessary to obtain an angiographic image of the right coronary artery by use of a catheter for right coronary artery, then replace the catheter with a catheter for left coronary artery, and obtain an angiographic image of the left coronary artery. Accordingly, the operation requires much labor and time, and exerts an increased burden on the patient.

In order to cope with this problem, a conventional catheter assembly has a structure based on a catheter having a shape called the left Judkins shape, in which a slidable outer jacket is fitted over the catheter, and the angular shape of the catheter assembly is varied by moving the outer jacket, so as to provide the catheter assembly with the functions of both a catheter having the left Judkins shape and a catheter having the right Judkins shape, whereby the need for the catheter replacing operation and the attendant operations is eliminated (see, for example, Japanese Patent Laid-open No. Hei 9-285546).

However, such a catheter assembly as this has the problem that, although the catheter assembly has a shape suitable for enabling the insertion thereof to a target site such as the right coronary artery and the left coronary artery, the shape is not suitable for holding (fixing) the catheter assembly in the target site. Therefore, there has been the problem that the catheter assembly inserted to the target site may slip off from the target site.

It is an object of the present invention to provide a catheter assembly which comprises, in a double form, two catheters different from each other in distal end portion shape, whereby it is possible to attain both the easiness of reaching the site in which the distal end portion is to be inserted and be made to indwell and enhancement of the fixing force for fixing the distal end portion in the site.

SUMMARY OF THE INVENTION

This invention provides a catheter assembly which comprises an outer catheter which comprises a distal end curved portion having a first curved shape, and an inner catheter which comprises a distal end curved portion having a second curved shape different from said first curved shape and which can be inserted into said outer catheter so that said distal end curved portion thereof is located in said distal end curved portion of said outer catheter and be withdrawn therefrom, wherein said distal end curved portion of said outer catheter is more flexible than said distal end curved portion of said inner catheter, and a distal end portion of said catheter assembly assumes a curved shape different from said first curved shape when said inner catheter is inserted in said outer catheter so that said distal end curved portion of said inner catheter is located in said distal end curved portion of said outer catheter.

This invention provides a catheter assembly comprising an outer catheter having an outer catheter main body, and an inner catheter having an inner catheter main body insertable in said outer catheter main body, wherein a distal end portion of said outer catheter main body and a distal end portion of said inner catheter main body have different curved shapes, said distal end portion of said outer catheter main body is more flexible than said distal end portion of said inner catheter main body, and said curved shape of said distal end portion of said outer catheter main body is deformed according to said curved shape of said distal end portion of said inner catheter main body when said inner catheter main body is inserted in said outer catheter main body so that their distal end portions overlap each other.

This invention provides a method of disposing a catheter in a cardiac blood vessel, said method comprising the steps of preparing a catheter assembly which comprises an outer catheter comprising a distal end curved portion having a first curved shape and an inner catheter comprising a distal end curved portion having a second curved shape different from said first curved shape and inserted in said outer catheter and said catheter assembly which has a distal end curved portion different from said first curved shape, disposing the distal end of said catheter assembly at a coronary artery port in an aortic, and withdrawing said inner catheter from said catheter assembly with said distal end thereof disposed at said coronary artery port, to thereby develop said first curved shape of said distal end curved portion of

BRIEF DESCRIPTION OF THE DRAWINGS

FIG. 2 is a partly omitted plan view showing the overall shape of an outer catheter constituting the catheter assembly according to one embodiment of the present invention.

FIG. 3 is a partly omitted plan view showing the overall shape of an inner catheter constituting the catheter assembly according to the embodiment of the present invention.

FIG. 4 is a partly omitted plan view showing the overall shape of the catheter assembly according to the embodiment of the present invention, in the condition where a guide wire is passed through the inside of the catheter assembly.

FIG. 5 is an illustration of a method of introducing the catheter assembly into a blood vessel according to the present invention.

FIG. 12 is a partly omitted plan view showing the overall shape of a catheter assembly according to a further embodiment of the present invention.

FIGS. 16A to 16C schematically illustrate a method of using the catheter assembly according to the present invention.

DETAILED DESCRIPTION OF THE PREFERRED EMBODIMENTS

Figure 1:
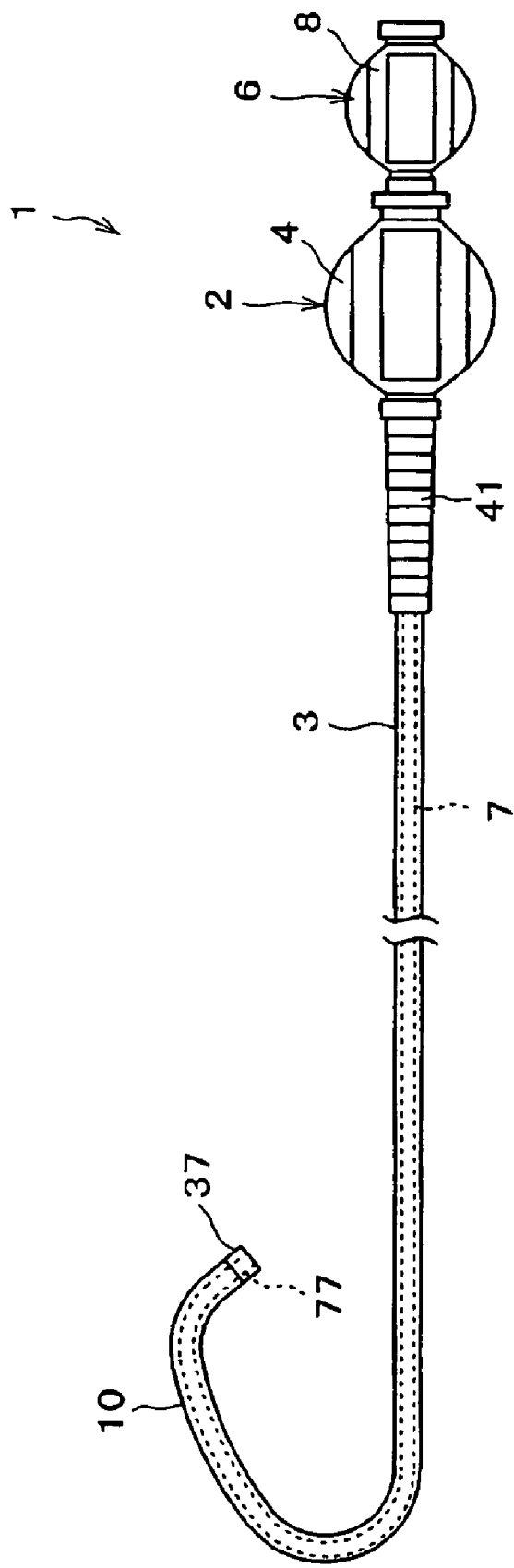
FIG. 1 is a partly omitted plan view showing the overall shape of a catheter assembly in its assembled state according to the present invention.

Now, the catheter assembly according to the present invention will be described in detail below, based on preferred embodiments shown in the accompanying drawings.

The catheter assembly 1 according to the present invention comprises an outer catheter 2 comprising a distal end curved portion 33 having a first curved shape, and an inner catheter 6 which comprises a distal end curved portion 73 having a second curved shape different from the first curved shape and is insertable into the outer catheter 2 so that distal end curved portion 73 is located in the distal end curved portion of the outer catheter 2 and can be withdrawn therefrom. The distal end curved portion 33 of the outer catheter 2 is more flexible than the distal end curved portion 73 of the inner catheter 6. A distal end portion of the catheter assembly 1, when the inner catheter 6 is inserted in the outer catheter 2 so that the distal end curved portion 73 of the inner catheter 6 is located in the distal end curved portion 33 of the outer catheter 2, assumes a curved shape different from the first curved shape.

First Embodiment

The present embodiment pertains to a catheter which is used as a guiding catheter for guiding a procedure catheter, for example, a balloon catheter for PTCA, or as an angiography catheter for injecting a contrast medium, and which is used for inserting such a catheter into the left coronary artery and setting the catheter to indwell there. Herein, description will be made by referring to the right side in FIG. 1 (and in FIGS. 2, 3, 4 and 7, also) as "the proximal end", the left side as "the distal end", the side closer to the proximal end as "proximal", and the side farther from the proximal end as "distal".

As shown in FIG. 1, the catheter assembly 1 according to the present invention comprises an outer catheter 2 and an inner catheter 6.

As shown in FIG. 2, the outer catheter 2 is composed of an outer catheter main body 3 having a lumen in which the inner catheter 6 can be inserted and can be withdrawn after insertion, and a hub 4 attached (fixed) to the proximal end of the outer catheter main body 3.

As shown in FIG. 3, the inner catheter 6 is composed of an inner catheter main body 7 which can be inserted into the outer catheter main body 3 and can be withdrawn after insertion, and a hub 8 attached (fixed) to the proximal end of the inner catheter main body 7.

When the inner catheter main body 7 is inserted into the proximal end side of the hub 4, starting from the distal end side of the inner catheter main body 7, and the hub 4 and the hub 8 are fitted to each other, a condition where the outer catheter 2 and the inner catheter 6 are assembled (hereinafter referred to simply as "the assembled condition") results, as shown in FIG. 1.

First, the outer catheter 2 will be described. The outer catheter main body 3 is composed of a flexible tube. The inside diameter of the lumen in the outer catheter main body 3 is not particularly limited, inasmuch as it is greater than the outside diameter of the inner catheter main body 7 so that the inner catheter main body 7 is inserted in the lumen. In consideration of a reduction in the diameter of the outer catheter main body 3, generally, the inside diameter of the lumen in the outer catheter main body 3 is preferably 3 mm or below, more preferably 2.5 mm or below, further preferably 2.0 mm or below.

As shown in FIG. 2, the outer catheter 2 comprises a distal end curved portion 33 having a first curved shape. Specifically, the outer catheter main body 3 comprises a proximal portion 31 and an intermediate portion 32 which extend substantially rectilinearly, and a distal end portion (in other words, the distal end curved portion) 33 extending from the intermediate portion 32 further toward the distal end and having a desired curved shape (the first curved shape), in this order from the proximal end side.

In the outer catheter in this embodiment, the distal end portion 33 comprises a curved portion 331 and a distal end portion 332. The curved portion 331, in plan view, is curved only in the same direction from the intermediate portion 32 and has such a looped shape as to intersect the intermediate portion 32 once. The distal end portion 332, in plan view, has a rectilinearly extending portion, extending in substantially the same direction as the longitudinal direction of the outer catheter main body 3 from the intersection between the curved portion 331 and the intermediate portion 32.

Incidentally, while the curved portion 331 intersects the intermediate portion 32 only once in the present embodiment, this shape is not limitative; the intersection may occur a number of times, inasmuch as the shape of the curved portion 331 promises a position maintaining property for maintaining the distal end portion 33 in the site in which the distal end portion 33 is to be inserted and be made to indwell.

The proximal portion 31 and the intermediate portion 32 are substantially rectilinear in shape in the condition where no external force is exerted thereon (specifically, in the natural condition where external forces such as bending, torsion, pulling, and compression are not exerted thereon). Incidentally, while the proximal portion 31 and the intermediate portion 32 are integral with each other, i.e., there is no boundary therebetween in the present embodiment, this form is not limitative; for example, the proximal portion 31 and the intermediate portion 32 may be composed of separate members, respectively.

The overall length of the proximal portion 31 and the intermediate portion 32, or the length from the proximal end of the outer catheter main body 3 to the curved portion 331, is not particularly limited. Generally, the length is preferably in the range of about 450 to 1500 mm, more preferably about 600 to 1200 mm. A further smaller length may be adopted in the cases of pediatric use or infant use.

The curved portion 331 is curved (bent) in a desired shape in the condition where no external force is exerted thereon (specifically, in the condition where external forces such as bending, torsion, pulling, and compression are not exerted thereon). Here, it is preferable that, let the average of the inside radius of curvature of the distal end portion 33 of the outer catheter main body 3 be R1 [mm] and let the maximum inside radius of the aortic arch 109 be D1 [mm], then the ratio R1/D1 is in the range of from 1.0 to 2.0.

If the ratio R1/D1 is too small, the area where the curved portion 331 makes contact with the inside wall of the aortic arch 109 is reduced, so that the position maintaining property for maintaining the distal end portion 33 in the indwelling site in the aortic arch 109 is lowered, and the curved portion 331 is liable to kink, possibly clogging the lumen 5 which will be described later. On the other hand, if the ratio R1/D1 is too large, the curved portion 331 would press the inside wall of the aortic arch 109 excessively, which may increase the burden on the patient.

Incidentally, the maximum inside radius of the aortic arch 109 herein means the inside radius in the vicinity of the inlet of the right or left coronary artery, and a specific value thereof is about 15 to 20 mm, though it differs from patient to patient.

The average R1 of the radius of curvature is not particularly limited; for the ratio R1/D1 to be within a desirable range, however, the average R1 is preferably in the range of about 25 to 60 mm, more preferably about 30 to 50 mm.

The length of the distal end portion 332 is not particularly limited, and is preferably in the range of about 1 to 10 mm, more preferably about 2 to 6 mm. When the length is in such a range, the distal end portion 332 can be favorably inserted into the left coronary artery.

Figure 6A:
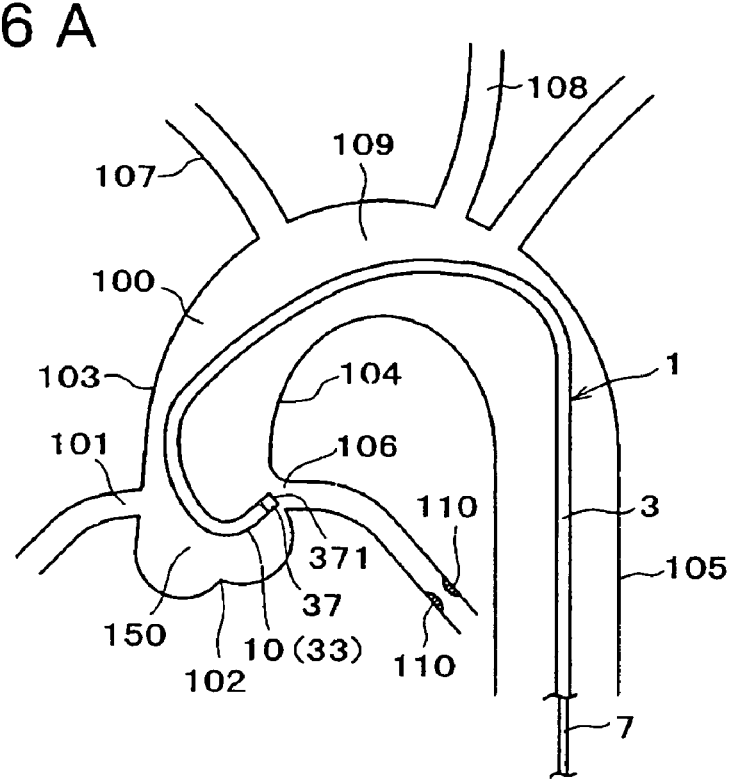
FIGS. 6A and 6B schematically illustrate a method of using the catheter assembly according to the present invention.
Figure 6B:
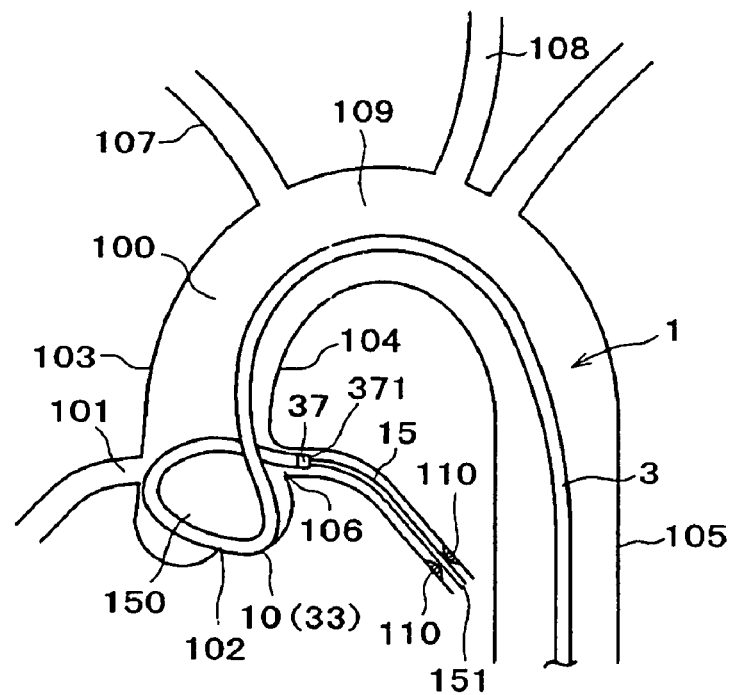

As shown in FIG. 6B, the distal end portion 33 having the curved shape as above makes contact with the inside wall of the aortic arch 109 in a wide area when the distal end portion 33 is held (made to indwell) in the left coronary artery port 106, to show a high position maintaining property.

Incidentally, the fixation, effected by the contact of the catheter with the inside surface of the site 150 between the left coronary artery port 106 and the right coronary artery port 101 (see FIG. 6), for example, when the distal end portion 33 of the catheter is let indwell in the site 150, is referred to as "backup". Further, a force for effecting the backup is referred to as "backup force".

Figure 7:
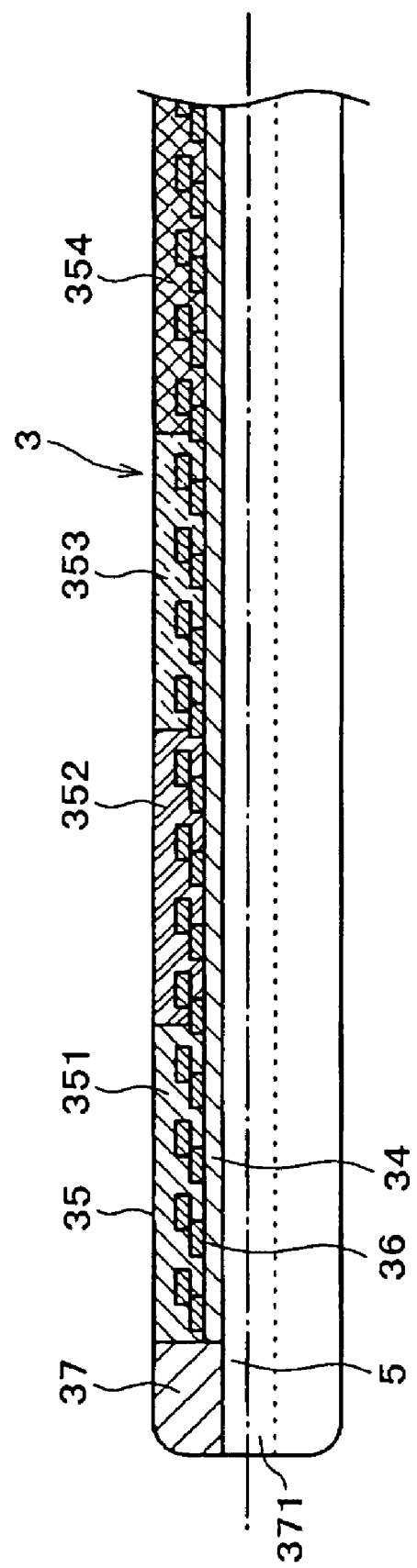
FIG. 7 is a vertical sectional view of a distal end portion of the outer catheter in the catheter assembly according to the present invention.

As shown in FIG. 7, the outer catheter main body 3 is composed of a laminate portion having three layers of an inner layer 34, an outer layer 35 and a reinforcement layer 36 located therebetween, and a soft tip 37 rich in flexibility which is provided at the distal end of the laminate portion. In addition, the outer catheter main body 3 is provided in a substantially central portion thereof with the lumen 5 over the entire length of the outer catheter main body 3. The lumen 5 opens at the distal end of the soft tip 37, thereby forming a distal end opening 371.

The outer layer 35 comprises a first region 351, a second region 352 located on the proximal end side of the first region 351, a third region 353 located on the proximal end side of the second region 352, and a fourth region 354 located on the proximal end side of the third region 353. Furthermore, the third region 353 is more flexible than the fourth region 354, the second region 352 is more flexible than the third region 353, and the first region 351 is more flexible than the second region 352.

Besides, examples of the material for constituting these regions (the first region 351, the second region 352, the third region 353, and the fourth region 354) include various thermoplastic elastomers based on styrene, polyolefin, polyurethane, polyester, polyamide, polybutadiene, trans-polyisoprene, fluororubber, chlorinated polyethylene or the like, and combinations (polymer alloys, polymer blends, laminates, etc.) of two or more of these thermoplastic elastomers.

Of the inner layer 34, the portion brought into contact with at least the inner catheter main body 7 when the inner catheter main body 7 is inserted in the lumen 5 (in the outer catheter main body 3) is preferably composed of a low-friction material.

Examples of the low-friction material include various resin materials such as polyamides, polyether-polyamides, polyester-polyamides, polyesters, polyurethane, soft polyvinyl chloride, ABS resin, AS resin, and fluororesins such as polytetrafluoroethylene.

The reinforcement layer 36 comprises a reinforcing material for reinforcing the outer catheter main body 3. Examples of the reinforcing material include those composed of filamentous materials, and those composed of meshed or netted materials. The filamentous materials have a helical structure or the like and are preferably formed of a metal, a hard resin or the like. Specific examples include those knitted from blank materials obtained by collapsing stainless steel wires into a flat shape so that the material thickness in the radial direction of the outer catheter main body 3 is made small.

In addition, the number of the layers constituting the outer catheter main body 3, the materials constituting the layers, the presence or absence of the reinforcing material, and the like may differ along the longitudinal direction of the outer catheter main body 3. For example, for enhancing the flexibility of the distal end side portion of the outer catheter main body 3, there can be adopted a structure in which either one portion of the curved portion 331 and the distal end portion 332 is reduced in the number of layers as compared with the other portion, or is formed of a more flexible material, or is formed by disposing a reinforcing material therein.

Incidentally, since the insertion of the catheter assembly 1 into a living body is conducted while confirming the position of the catheter assembly 1 under radioparency, it is preferable that a radiopaque material (X-ray contrast medium) is blended in the material constituting the outer layer 35. Examples of the radiopaque material which can be used include barium sulfate, bismuth oxide, tungsten, and the like. Furthermore, the ratio of the blended amount of the radiopaque material based on the amount of the materials constituting the outer layer 35 is preferably in the range of 30 to 80 wt. %.

In addition, the radiopaque material may not necessarily be present over the entire length of the outer catheter main body 3; namely, the radiopaque material may be present in a part of the outer catheter main body 3, for example, either one of the curved portion 331 and the distal end portion 332.

Besides, the portion of the inner layer 34 which makes contact with the inner catheter main body 7 is preferably formed of a low-friction material as above-mentioned, but this configuration is not limitative; for example, the inner layer 34 may entirely be formed of a low-friction material.

The soft tip 37 is composed of a soft material. This ensures that, at the time of inserting the catheter assembly 1 in the assembled state into a living body, the damage to the blood vessels by the distal end of the outer catheter main body 3 can be prevented more securely.

Examples of the material for constituting the soft tip 37 include various rubber materials such as natural rubber, isoprene rubber, butadiene rubber, chloroprene rubber, silicone rubbers, fluororubbers, styrene-butadiene rubber, etc., and various thermoplastic elastomers based on styrene, polyolefin, polyurethane, polyester, polyamide, polybutadiene, trans-polyisoprene, fluororubber, chlorinated polyethylene or the like.

The hub 4 is attached (fixed) to the proximal end of the outer catheter main body 3. The hub 4 is provided therein with a lumen communicated with the lumen 5. The lumen has an inside diameter nearly equal to the inside diameter of the lumen 5, and is continuous with the inside surface of a proximal end portion of the lumen 5 without any step or the like therebetween.

Through the hub 4, it is possible to insert an elongate body (filamentous body) such as a guide wire, catheters (for example, a balloon catheter for PTCA), an endoscope, an ultrasonic probe, a temperature sensor, etc., and it is possible to inject various liquids such as a contrast medium (X-ray contrast medium), a liquid medicament, physiological saline, etc, or withdraw the elongate body. In addition, the hub 4 can be connected to other appliances in the case of, for example, blood pressure measurement or the like.

Besides, the portion of connection between the outer catheter main body 3 and the hub 4 is provided with a cover member (anti-kink protector) 41 having a reinforcing function. This prevents more effectively the portion from kinking.

Next, the inner catheter 6 will be described.

The inner catheter 6 comprises a distal end curved portion having a second curved shape different from the first curved shape of the outer catheter 2, and can be inserted into the outer catheter 2 so that the distal end curved portion thereof is located in the distal end curved portion of the outer catheter 2 and be withdrawn therefrom.

Specifically, the inner catheter 6 comprises an inner catheter main body 7, and a hub 8 provided at the proximal end of the inner catheter main body 7.

The inner catheter main body 7 is composed of a flexible tube. The outside diameter of the inner catheter main body 7 is not particularly limited; in consideration of a reduction in the diameter of the outer catheter main body 3, generally, the outside diameter of the inner catheter main body 7 is preferably 2.1 mm or below, more preferably 1.8 mm or below, and further preferably 1.5 mm or below. Furthermore, it is preferable that the ratio of the outside diameter of the inner catheter main body 7 to the inside diameter of the outer catheter main body 3 mentioned above is in the range of from 0.9 to 0.99.

As shown in FIG. 3, the inner catheter main body 7 comprises a proximal portion 71 and an intermediate portion 72 which extend substantially rectilinearly, and a distal end portion (in other words, the distal end curved portion) 73 which extends further toward the distal end from the intermediate portion 72 and assumes a desired curved shape (the second curved shape), in this order from the proximal end side.

The distal end portion 73 comprises a curved portion 731. The curved portion 731, in plan view, is curved from the intermediate portion 72 only in the same direction and has such a shape as not to intersect the intermediate portion 32.

The proximal portion 71 and the intermediate portion 72 are substantially rectilinear in shape in the condition where no external force is exerted thereon (specifically, in the natural condition where external forces such as bending, torsion, pulling, and compression are not exerted thereon). In addition, the structure in which the proximal portion 71 and the intermediate portion 72 are integral with each other without any boundary therebetween as in this embodiment is not limitative. For example, the proximal portion 71 and the intermediate portion 72 may be composed of separate members, respectively.

The overall length of the proximal portion 71 and the intermediate portion 72, namely, the length from the proximal end of the inner catheter main body 7 to the curved portion 731 is not particularly limited. Generally, the length is preferably in the range of about 450 to 1500 mm, more preferably about 600 to 1200 mm. Besides, the length may be further smaller in the cases of pediatric use or infant use.

The curved portion 731 is curved (bent) in a desired shape in the condition where no external force is exerted thereon (specifically, in the natural condition where external forces such as bending, torsion, pulling, and compression are not exerted thereon). Here, let the average of the radius of curvature of the distal end portion 73 of the inner catheter main body 7 be R2 [mm] and let the maximum inside radius of the aortic arch 109 be D1 [mm], then the ratio R2/D1 is in the range of from 0.3 to 1.0. This permits the distal end portion 73 to reach (be inserted into) the left coronary artery port 106 smoothly.

The average R2 of the radius of curvature is not particularly limited; for attaining the ratio R2/D1 within the preferred range, the average R2 of the radius of curvature is preferably in the range of about 5 to 25 mm, more preferably about 10 to 20 mm.

As shown in FIG. 6A, the curved shape of the distal end portion 73 of the inner catheter main body 7 as above-mentioned is such a shape as to permit the distal end portion 73 to reach (be inserted into) the left coronary artery port 106 smoothly.

Incidentally, to insert the distal end portion of the catheter into, for example, the left coronary artery port 106 or the right coronary artery port 101 will be referred to as "to engage" or "engagement".

The inner catheter main body 7 is provided at the distal end portion 73 thereof with a soft tip 77 which is rich in flexibility. In addition, the inner catheter main body 7 is provided in a nearly central portion thereof with a lumen 9 extending over the entire length thereof. The lumen 9 opens at the distal end of the soft tip 77.

The soft tip 77 is composed of a soft material. This ensures that, at the time of inserting the catheter assembly 1 in the assembled condition into a living body, the damage to the blood vessels by the distal end of the inner catheter main body 7 can be prevented more securely.

Examples of the material for constituting the soft member include the same materials as mentioned above for the soft tip 37.

Incidentally, the inner catheter main body 7 may be composed in the above-mentioned laminate structure or a laminate structure free of the reinforcement layer, or may be composed of a single layer.

Examples of the material for constituting the inner catheter main body 7 include various resin materials such as polyamides, polyether-polyamides, polyester-polyamides, polyesters such as polyethylene terephthalate and polybutylene terephthalate, polyurethane, polyvinyl chloride, ABS resin, AS resin, fluororesin such as polytetrafluoroethylene, polyester elastomers, polyurethane elastomers, polyolefins, etc.

The hub 8 is attached (fixed) to the proximal end of the inner catheter main body 7. The hub 8 is provided therein with a lumen communicated with the lumen 9. The lumen has an inside diameter nearly equal to the inside diameter of the lumen 9, and is continuous with the inside surface of a proximal end portion of the lumen 9 without any step or the like therebetween.

Through the hub 8, it is possible to insert an elongate body (filamentous body) such as a guide wire, catheters (for example, a balloon catheter for PTCA), an endoscope, an ultrasonic probe, a temperature sensor, etc., and it is possible to inject various liquids such as a X-ray contrast medium, a liquid medicament, physiological saline, etc, or withdraw the elongate body. In addition, the hub 8 can be connected to other appliances in the case of, for example, blood pressure measurement or the like.

Incidentally, the portion of connection between the inner catheter main body 7 and the hub 8 may be provided with a cover member (anti-kink protector) having a reinforcing function.

In addition, the outer catheter and the inner catheter may be provided with a movement preventive mechanism for preventing the inner catheter from being released from the outer catheter and for restraining the inner catheter from moving in the outer catheter. Provision of such a movement preventive mechanism ensures that, when the catheter assembly is operated by gripping the outer catheter portion, the inner catheter favorably follows up to the movement of the outer catheter, and movements of the outer catheter alone can be prevented from occurring. The movement preventive mechanism may be one using a frictional force generated by the process in which the distal end curved portion of the outer catheter is rectified by the distal end curved portion of the inner catheter inserted therein, or may be one in which both the outer catheter hub 4 and the inner catheter hub 8 are respectively provided with engaging mechanisms. Preferably, the engaging mechanisms provided at the outer catheter hub 4 and the inner catheter hub 8 are such that the inner catheter hub is provided at its distal end portion with an engaging portion for engagement with a proximal end portion of the outer catheter hub, or are further such that the cover member (anti-kink protector) having the reinforcing function mentioned above is engaged with the proximal end portion of the outer catheter hub.

Next, the relationship in flexibility (rigidity) between the distal end portion 33 of the outer catheter main body 3 and the distal end portion 73 of the inner catheter main body 7 will be described.

In the catheter assembly 1 according to the present invention, the distal end portion 73 of the inner catheter 6 is higher in rigidity than the distal end portion 33 of the outer catheter 2. In other words, the distal end curved portion 33 of the outer catheter 2 is more flexible than the distal end curved portion 73 of the inner catheter 6. Therefore, when the distal end portion 73 (the inner catheter main body 7) is inserted in the distal end portion 33 (the outer catheter main body 3), the distal end portion 33 of the outer catheter 2 is rectified by the shape of the distal end portion 73 of the inner catheter 6 (in other words, it depends on the shape of the distal end portion 73), and the shape of the distal end portion 33 is changed in accordance to the shape of the distal end portion 73.

Incidentally, the relationship in bending stress between the distal end portion 33 and the distal end portion 73 is preferably as follows.

First, let the bending stress on the distal end portion 33 of the outer catheter main body 3 in water at a temperature of 37 degree C. be σ1 [gf] and let the bending stress on the distal end portion 73 of the inner catheter main body 7 in water at a temperature of 37 degree C. be σ2 [gf], then the bending stress σ1 is preferably in the range of 10 to 400 gf, and the bending stress σ2 is preferably in the range of 20 to 500 gf.

In addition, the ratio σ2/σ1 of the bending stress on the distal end portion 73 in water at a temperature of 37 degree C. to the bending stress on the distal end portion 33 in water at a temperature of 37 degree C. is preferably in the range of from 1.05 to 3.0. From this relationship it can be said that the distal end portion 33 is richer in flexibility than the distal end portion 73. Namely, the distal end portion 73 is higher in rigidity than the distal end portion 33.

Now, the bending stresses will be described by giving a specific example.

As the materials for constituting the outer catheter 2, a polyester elastomer [PELPRENE (registered trademark) P280B, produced by Toyobo Co., Ltd.] was used for the outer layer 35, polytetrafluoroethylene was used for the inner layer 34, and a blank material braided from flat sheets of stainless steel was used for the reinforcement layer 36.

As the material for constituting the inner catheter 6, a single layer of polybutylene terephthalate was used.

By using these materials, the outer catheter and the inner catheter were produced so as to have the outside diameters and inside diameters as shown in Table 1.

Figure 17:
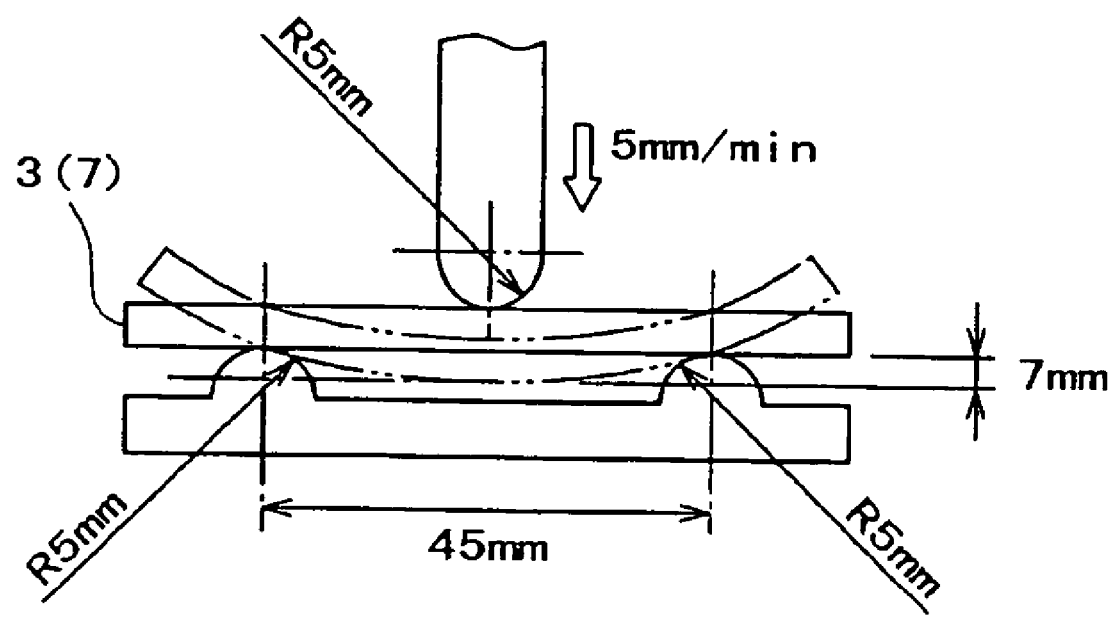
FIG. 17 is a schematic illustration of the three-point bending method.

In addition, for each of the outer catheter 2 and the inner catheter 6, the bending stress was measured by the method illustrated in FIG. 17. In the measurement, the bending stress was measured using an autograph by the three-point bending method in water at 37 degree C. under the conditions of a fulcrum-to-fulcrum distance of 45 mm, a pushing-in speed of 5 mm/min, and a deflection amount of 7 mm.

TABLE 1

|  | Outside Diameter (mm) | Inside Diameter (mm) | Bending Stress (gf) |
| --- | --- | --- | --- |
| Outer Catheter | 2.06 | 1.85 | 71 |
| Inner Catheter | 1.77 | 1.10 | 91 |

As shown in Table 1, the bending stress σ1 was 71 gf, and the bending stress σ2 was 91 gf. This leads to σ2/σ1=1.28.

The catheter assembly 1, in the assembled condition, comprising the above-mentioned outer catheter 2 and inner catheter 6 will be described below.

First, the method of assembling the catheter assembly 1 will be described.

The inner catheter main body 7 is inserted into the hub 4, starting from the side of the soft tip 77. As the insertion is continued further, the inner catheter main body 7 is gradually inserted into the outer catheter main body 3. When the insertion is continued until the hub 4 and the hub 8 fits to each other, the distal end portions (the distal end portion 33 and the distal end portion 73) of the outer catheter 3 and the inner catheter 7 come to overlap each other. In this instance, a distal end portion of the soft tip 37 of the outer catheter 2 and a distal end portion of the soft tip 77 of the inner catheter 6 coincide substantially with each other, resulting in the catheter assembly 1 in the assembled condition.

In the catheter assembly 1 assembled in this manner, the distal end portion 73 of the inner catheter is higher in rigidity than the distal end portion 33 of the outer catheter, as has been described above, and the distal end portions overlap each other in this assembled condition. Therefore, the shape of the member higher in rigidity predominates, i.e., the distal end portion 10 of the catheter assembly 1 in the assembled condition assumes a shape like the distal end portion 73 (a shape similar to the shape of the distal end portion 73).

Next, the condition where at least the distal end portion 73 has been withdrawn from the distal end portion 33, starting from the assembled condition, will be described.

In this condition, the distal end portion 73 is not present inside the distal end portion 33 and the lumen 5 is hollow, so that the distal end portion 33 is in the condition where no external force is exerted thereon from the inner catheter main body 7 (specifically, in the natural condition where external forces such as bending, torsion, pulling, and compression are not exerted thereon). Therefore, the curved shape of the distal end portion 33 has returned substantially to the original curved shape in the condition where no external force is exerted.

Besides, at the time of using the catheter assembly 1 in the assembled condition, a substantially rectilinear guide wire 13 is used together with the catheter assembly 1.

As shown in FIG. 4, the guide wire 13 is inserted into the lumen 9 of the inner catheter main body 7. The guide wire 13 is higher in rigidity than the inner catheter 6 (the distal end portion 73); therefore, upon the insertion of the guide wire 13, the catheter assembly 1 in the assembled condition assumes a substantially rectilinear shape.

Next, one example of the method of using the catheter assembly 1 according to the present invention will be described.

As shown in FIG. 5, by using the Seldinger technique, a catheter introducer 11 is made to puncture an artery (introduction site) 14 such as, for example, the right femoral artery, the right brachial artery or the right radial artery, then the catheter assembly 1 according to the present invention with the guide wire 13 inserted in the lumen 9 is inserted into a sheath 12 of the catheter introducer 11, and, while causing the guide wire 13 to proceed, the distal end of the catheter assembly 1 is inserted through a distal end opening 121 of the sheath 12 into the artery 14.

Next, the catheter assembly 1 in the assembled condition is gradually fed forwards while causing the guide wire 13 to proceed in the direction of the arrow in FIG. 5, toward the site in which the distal end portion 10 of the catheter assembly 1 is to be inserted and be made to indwell (for example, the right coronary artery, the left coronary artery, the left ventricle, or the like). In order that the distal end portion 10 passes through curved portions (bent portions) of blood vessels smoothly and in order for appropriate selection of a branch of blood vessel, operations composed of an appropriate combination of projecting and retracting movements of the guide wire 13 relative to the catheter assembly 1; forward and backward movements of the catheter assembly 1, and rotations of the catheter assembly 1 are carried out.

The operations (maneuver) at the time of inserting the distal end portion 10 of the catheter assembly 1 in the assembled condition into the left coronary artery will be described in detail, based on FIGS. 6A and 6B. Incidentally, these operations are carried out while confirming the position and posture of the catheter assembly 1 under radioparency.

The catheter introducer 11 is made to puncture the femoral artery, then the catheter assembly 1 with the guide wire 13 inserted in the lumen 9 of the catheter assembly 1 (the inner catheter main body 7) in the assembled condition is inserted into the catheter introducer 11, and, while causing the guide wire 13 to proceed, the distal end portion 10 of the catheter assembly 1 is advanced through the abdominal aorta 105 to the ascending aorta 100. When the distal end portion 10 is located about 10 cm above the left coronary artery port 106, the advancing of the catheter assembly 1 is stopped, and the guide wire 13 is withdrawn, to permit the shape of the distal end portion 10 to return to the curved shape (the natural condition) of the catheter assembly 1.

Next, while confirming the position of the distal end of the catheter assembly 1 in the assembled condition, the catheter assembly 1 is slowly advanced, upon which the distal end portion 10 (the distal end portion 33) of the catheter assembly 1 is moved downwards while making contact with the left inside wall 104 of the ascending aorta 100, to be inserted into the left coronary artery port 106. As has been described above, the shape of the distal end portion 10 (the distal end portion 33) in this instance is a shape suitable for easy engagement.

Incidentally, when the distal end portion 10 of the catheter assembly 1 in the assembled condition is directed to the side opposite to the left coronary artery port 106, the catheter assembly 1 is slightly rotated counterclockwise so as to direct the distal end portion 10 of the catheter assembly 1 toward the left coronary artery port 106, and then the distal end portion 10 is slowly advanced. By this operation, the distal end portion 10 is easily inserted (engaged) into the left coronary artery port 106.

Next, the inner catheter 6 is withdrawn from the catheter assembly 1 in the assembled condition, to permit the shape of the distal end portion 33 of the outer catheter 2 to return to its preformed curved shape (the natural condition). Since the curved shape is a shape suitable for backup, the distal end portion 33 is firmly fixed to the left coronary artery port 106.

After the distal end portion 33 is fixed to the left coronary artery port 106 by the above operations, a connector of a contrast medium injecting appliance which is not shown is connected to the hub 4, and a contrast medium is injected. The contrast medium thus injected passes through the hub 4 and the lumen 5, and is jetted through the distal end opening 371 of the soft tip 37 into the left coronary artery. Through this operation, imaging of a constricted portion (stenosis portion) 110 is performed.

In this case, incidentally, a reaction force due to the jetting of the contrast medium is exerted on the distal end portion 33 (the outer catheter main body 3). However, since a sufficient backup force is being obtained as above-mentioned, the distal end portion 33 is prevented from slipping off from the left coronary artery port 106.

Next, the connector of the contrast medium injecting appliance is removed from the hub 4. Thereafter, a procedure catheter such as a balloon catheter 15 for PTCA is inserted through the hub 4 and the lumen 5, and a distal end portion 151 of the PTCA balloon catheter 15 is projected via the distal end opening 371. Further, the distal end portion 151 is advanced to the constricted portion (stenosis portion) 110 present in the left coronary artery, and a dilation treatment is performed.

In this case, incidentally, a reaction force due to the insertion of the PTCA balloon catheter 15 into the left coronary artery port 106 is exerted on the distal end portion 33 (the outer catheter main body 3). However, the distal end portion 33 can be prevented from slipping off from the left coronary artery port 106, since a sufficient backup force is being obtained, in the same manner as above.

Here, appropriate combinations of the outer catheter 2, the inner catheter 6 and the guide wire 13 are evaluated. The items of evaluation are the reaching performance for the distal end portion 10 to reach the site (the left coronary artery port 106) in which the distal end portion 10 is to be inserted and be made to indwell, the easiness of engagement in the site, and the position holding performance (assuredness of backup) in the site. The results of evaluation for the respective evaluation items are shown in Table 2.

In Table 2, symbol A represents "extremely good", B represents "good" or "possible", and C represents "not conducted" or "difficult"

Besides, in Table 2, O represents the outer catheter 2, I represents the inner catheter 6, GW represents the guide wire 13, and + represents combination of the members (one is inserted in the other).

As seen from the above-mentioned legend, case No. 1 in Table 2 is the case where the guide wire 13 is inserted in the catheter assembly 1 in the assembled condition, case No. 2 is the case where the guide wire 13 is withdrawn from the combination of case No. 1 (that is, the case of using only the catheter assembly 1 in the assembled condition), case No. 3 is the case where the inner catheter 6 is withdrawn from the combination of case No. 2 (that is, the case of using only the outer catheter 2), and case No. 4 is the case where the guide wire 13 is inserted in the outer catheter 2.

TABLE 2

|  | Case No. | | | |
| --- | --- | --- | --- | --- |
|  | No. 1 | No. 2 | No. 3 | No. 4 |
| Combination | O + I + GW | O + I | O | O + GW |
| Reaching | A | C | C | B |
| Engagement | C | A | B | C |
| Position Holding | C | B | A | C |

From Table 2 it is seen that case No. 1 is excellent in reaching performance, case No. 2 gives a certain degree of position holding performance and an extremely easy engagement, and case No. 3 results in that engagement is possible and the position holding performance is extremely excellent.

Comparison between case No. 2 and case No. 3 shows that the catheter assembly 1 in the assembled condition with the shape of the distal end being similar to the shape of the distal end portion 73 (case No. 2) is superior in the easiness of engagement, whereas the use of only the outer catheter 2 with the shape of the distal end being suitable for fixation (case No. 3) is superior in the position holding performance.

Thus, the catheter assembly 1 according to the present invention is advantageous in that the shape of the distal end portion 10 (the distal end portion 33) can be appropriately changed to either that of the inner catheter or to that of the outer catheter by inserting the inner catheter main body 7 into the outer catheter main body 3 or withdrawing the inner catheter main body 7. In other words, at the time of engagement and at the time of fixation, a distal end shape suitable for the operation can be selected. Accordingly, both easiness of engagement and assuredness of backup can be attained when needed, while using the single catheter assembly 1. Namely, the easiness of engagement and the assuredness of backup can both be attained.

Second Embodiment

The present embodiment pertains to a catheter which is similar to that in the first embodiment above and which is to be inserted into and be made to indwell in the right coronary artery.

Figure 8:
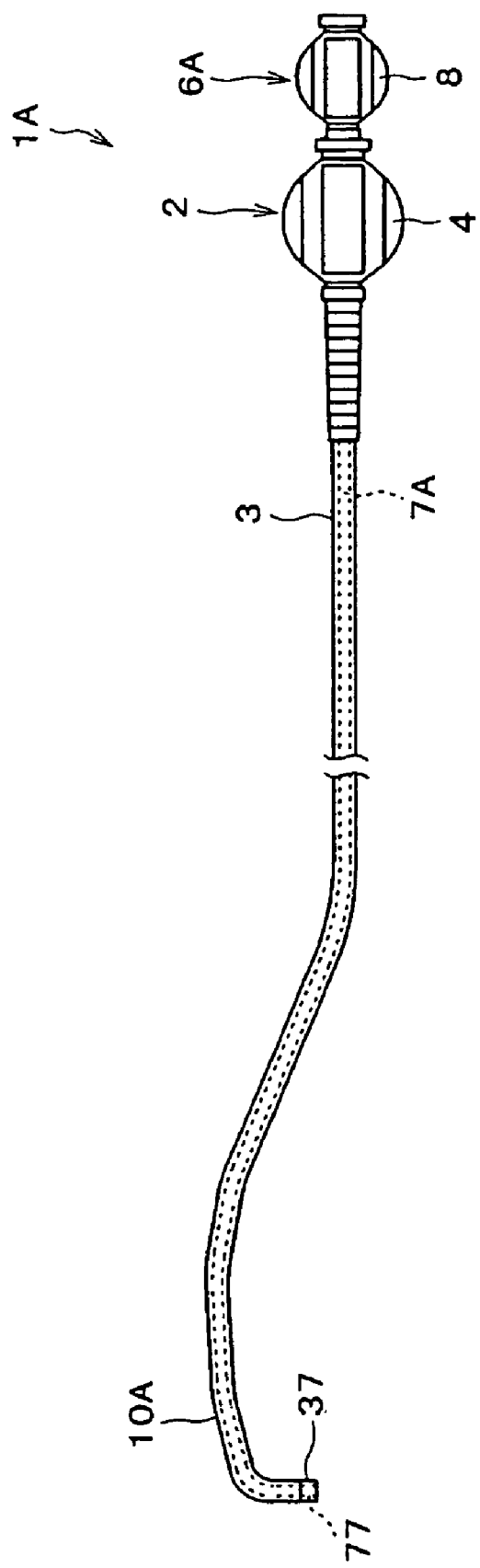
FIG. 8 is a partly omitted plan view showing the overall shape of a catheter assembly according to another embodiment of the present invention.
Figure 9:
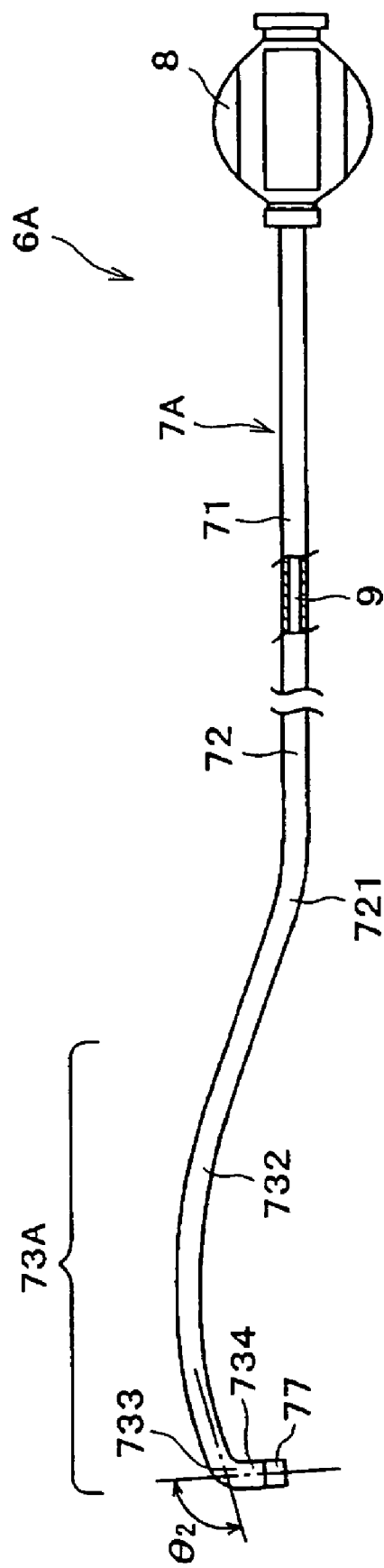
FIG. 9 is a partly omitted plan view showing the overall shape of an inner catheter constituting the catheter assembly according to another embodiment of the present invention.
Figure 10:
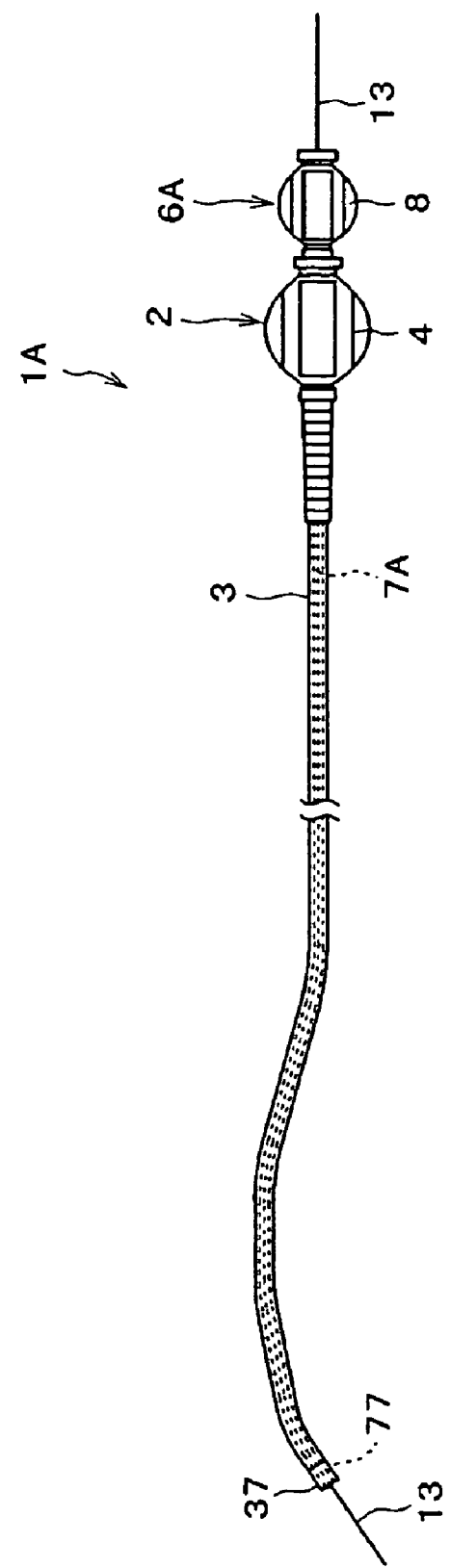
FIG. 10 is a partly omitted plan view showing the overall shape of the catheter assembly according to the present invention, in the condition where a guide wire is passed through the inside of the catheter assembly.
Figure 11A:
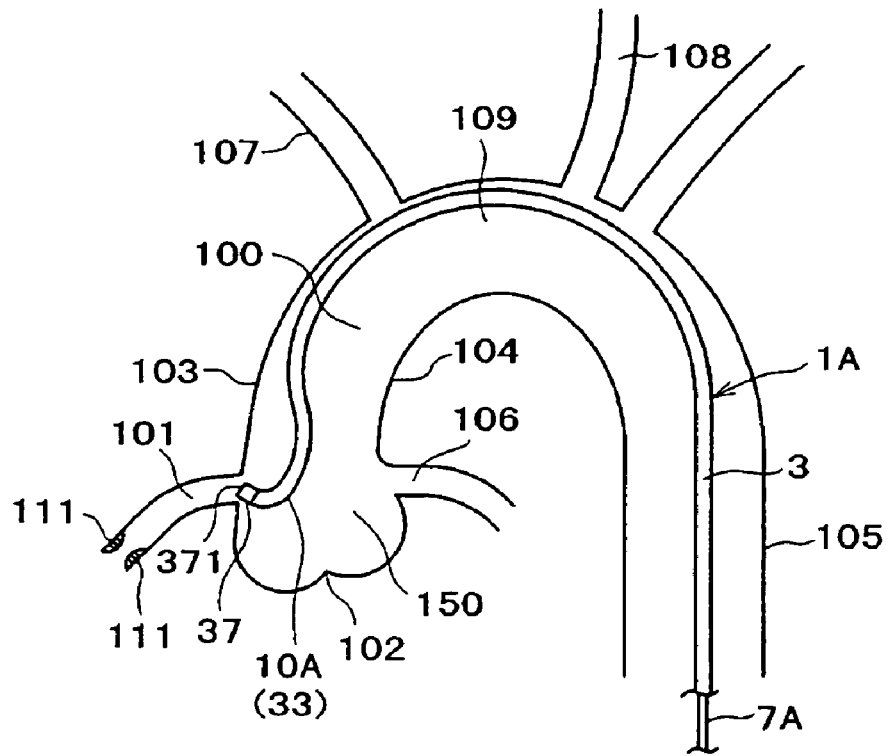
FIGS. 11A and 11B schematically illustrate a method of using the catheter assembly according to the present invention.
Figure 11B:
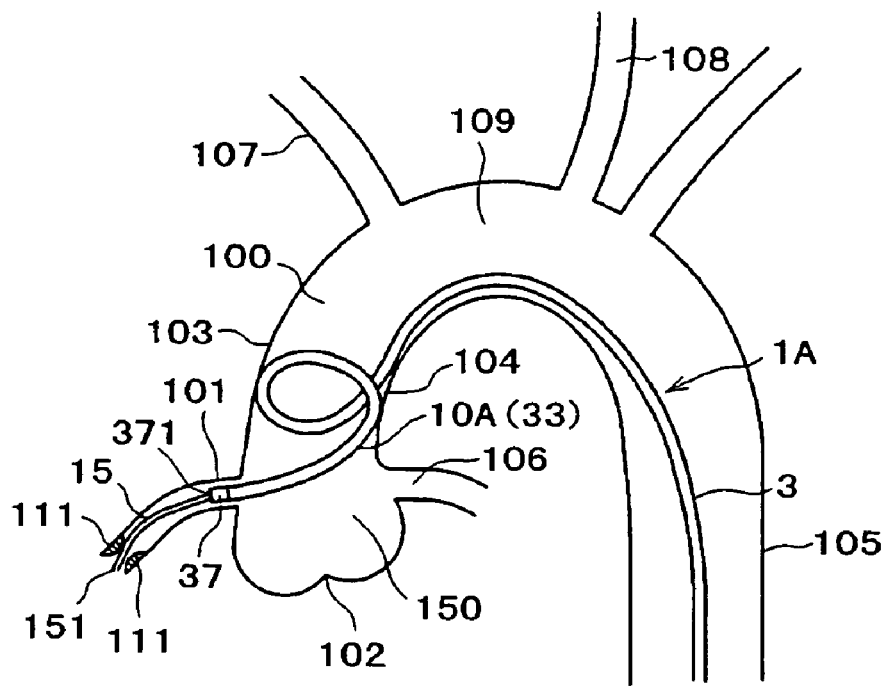

FIG. 8 is a partly omitted plan view showing the overall shape of a catheter assembly according to another embodiment of the present invention, FIG. 9 is a partly omitted plan view showing the overall shape of an inner catheter constituting the catheter assembly according to another embodiment of the present invention, FIG. 10 is a partly omitted plan view showing the overall shape of the catheter assembly according to the present invention, in the condition where a guide wire is passed through the inside of the catheter assembly, and FIGS. 11A and 11B schematically illustrate a method of using the catheter assembly according to the present invention. Herein, the right side in FIG. 8 (and in FIGS. 9 and 10 also) will be referred to as "the proximal end", the left side as "the distal end", the side closer to the proximal end as "proximal", and the side farther from the proximal end as "distal".

Now, the second embodiment of the catheter assembly according to the present invention will be described below referring to these figures, the description being centered on the differences from the above-described first embodiment. The same points as in the first embodiment should be understood by referring to the above description, and, therefore, description of these points will be omitted.

The catheter assembly according to this embodiment shown in FIG. 8 is the same as in the first embodiment, except for the configuration of the inner catheter. The catheter assembly 1A according to the present invention comprises an outer catheter 2 and an inner catheter 6A. Of these members, the outer catheter 2 is the same as that in the first embodiment.

As shown in FIG. 9, the inner catheter 6A is composed of an inner catheter main body 7A which can be inserted in the outer catheter main body 3, and a hub 8 attached (fixed) to the proximal end of the inner catheter main body 7A.

The inner catheter main body 7A comprises a proximal portion 71 and an intermediate portion 72 which extend substantially rectilinearly, a curved portion 721 slightly curved relative to the intermediate portion 72, and a distal end portion 73A curved in the direction opposite to the curved portion 721, in this order from the proximal end side.

The distal end portion 73A comprises a first curved portion 732, a second curved portion 733, and a distal end portion 734.

The first curved portion 732 assumes a shape gradually curved in the direction opposite to the curved portion 721, in the condition where no external force is exerted thereon.

The second curved portion 733 assumes a shape rapidly curved (bent) at a predetermined angle in the same direction as the first curved portion 732. This shape is curved (bent) in the same condition as above. The angle (the angle formed between the first curved portion 732 and the distal end portion 734) θ2 of the second curved portion 733 is not particularly limited, and is in the range of 60 to 120°, preferably 80 to 100°.

The distal end portion 734 extends substantially rectilinearly from the second curved portion 733. The length of the distal end portion 734 is not particularly limited, and is preferably in the range of about 1 to 15 mm, more preferably about 2 to 10 mm.

Such a shape of the distal end portion 73A is a shape suitable for easy engagement of the distal end portion 73A with the right coronary artery port 101.

As shown in FIG. 10, the catheter assembly 1A is used after a guide wire 13 is inserted in the catheter assembly 1A in the assembled condition. Incidentally, the shape of the catheter assembly 1A in the assembled condition in this instance is roughly rectilinear.

Next, one embodiment of the method of using the catheter assembly 1A according to the present invention will be described.

Here, as in the above-described first embodiment, the operations (maneuver) at the time of inserting the distal end portion 10A of the catheter assembly 1A in the assembled condition into the right coronary artery will be described in detail, based on FIGS. 11A and 11B.

A catheter introducer 11 is made to puncture the femoral artery, the guide wire 13 is inserted in a lumen 9 of the catheter assembly 1A (inner catheter main body 7A) in the assembled state, the catheter assembly 1A in this condition is inserted into the catheter introducer 11, and then, while causing the guide wire 13 to proceed, the distal end portion 10A of the catheter assembly 1A is advanced through the abdominal aorta 105 to the ascending aorta 100. Thereafter, the guide wire 13 is withdrawn, thereby permitting the shape of the distal end portion 10A to return to the original curved shape (the natural condition) of the catheter assembly 1A.

Next, the catheter assembly 1A in the assembled condition is once slowly advanced to the vicinity of the aortic valve 102 deeper than the right coronary artery port 101, so as to bring the distal end of the catheter assembly 1A into contact with the right inside wall 103 of the ascending aorta 100, and the catheter assembly 1A is slowly pulled backwards while turning it clockwise, whereby the distal end portion 10A (the distal end portion 33) of the catheter assembly 1A is inserted into the right coronary artery port 101. Incidentally, the shape of the distal end portion 10A is roughly the same with the shape of the distal end portion 73A, which promises easy engagement.

Thereafter, in the same manner as in the first embodiment, the inner catheter 6A is withdrawn from the catheter assembly 1A in the assembled condition, to cause backup of the distal end portion 33 in the right coronary artery port 101.

Further, the distal end portion 33 is fixed in the right coronary artery port 101, then, in the same manner as in the first embodiment, a distal end portion 151 of a balloon catheter 15 for PTCA is advanced to a constricted portion (stenosis portion) 111 present in the right coronary artery, and a dilation treatment is performed.

Thus, also in the catheter assembly 1A according to the second embodiment, the distal end portion 10A (the distal end portion 33) can be appropriately changed, in the same manner as in the first embodiment. In other words, at the time of engagement and at the time of fixation, a shape suitable for the operation can be selected, whereby both easiness of engagement and assuredness of backup can be attained when needed, while using the single catheter assembly 1A. Namely, the easiness of engagement and the assuredness of fixation can both be attained.

Third Embodiment

The present embodiment pertains to a catheter similar to that in the above-described first embodiment, which is to be inserted into and be made to indwell in the left common carotid artery or the right common carotid artery.

Figure 13:
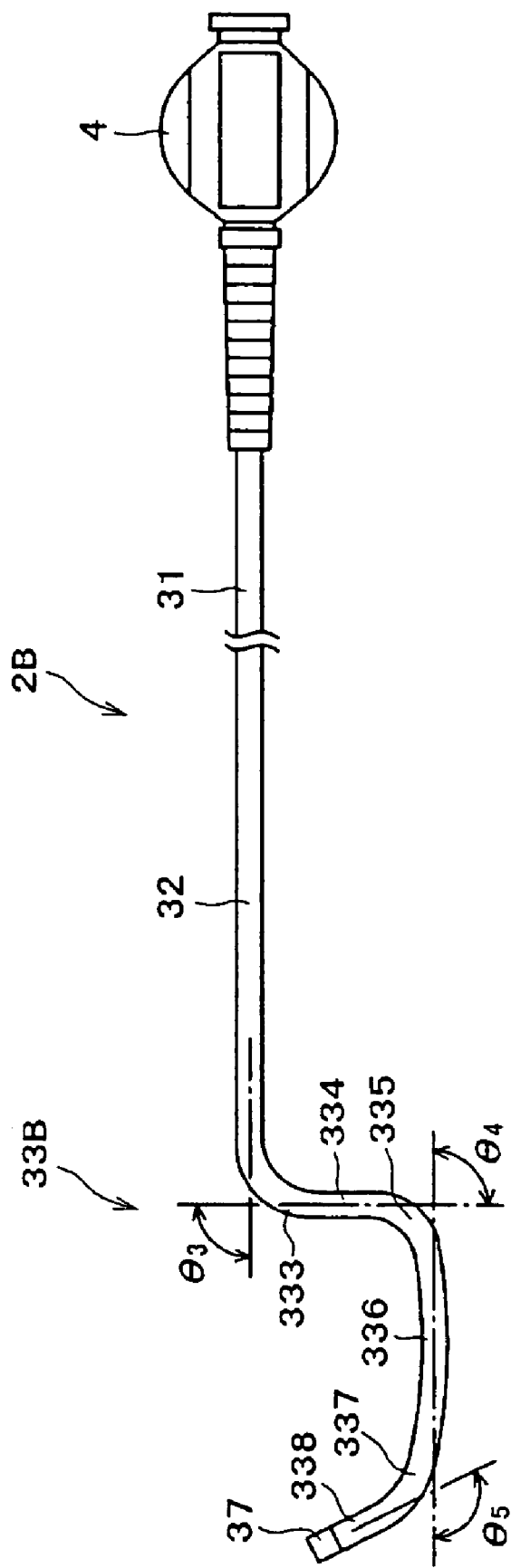
FIG. 13 is a partly omitted plan view showing the overall shape of an outer catheter constituting the catheter assembly according to the further embodiment of the present invention.
Figure 14:
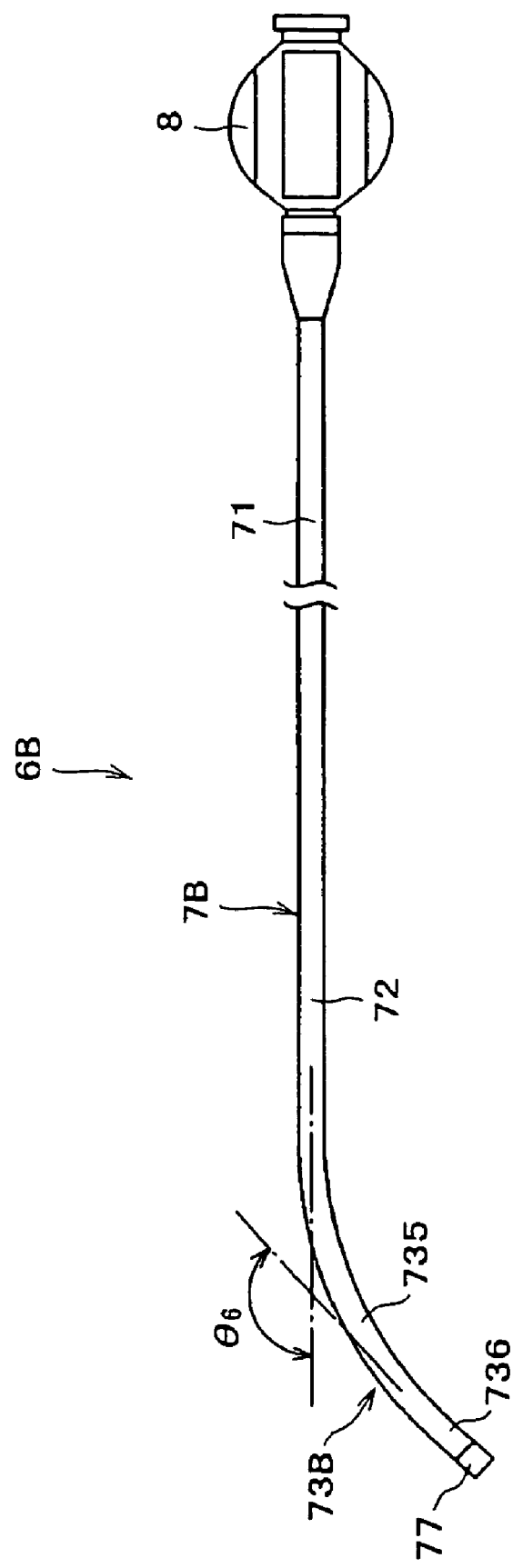
FIG. 14 is a partly omitted plan view showing the overall shape of an inner catheter constituting the catheter assembly according to the further embodiment of the present invention.
Figure 15A:
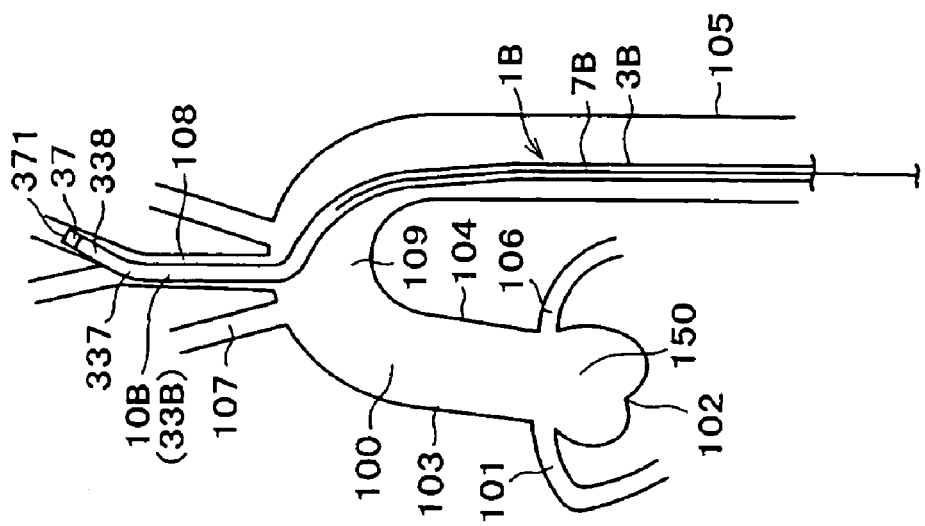
FIGS. 15A to 15C schematically illustrate a method of using the catheter assembly according to the present invention.
Figure 15B:
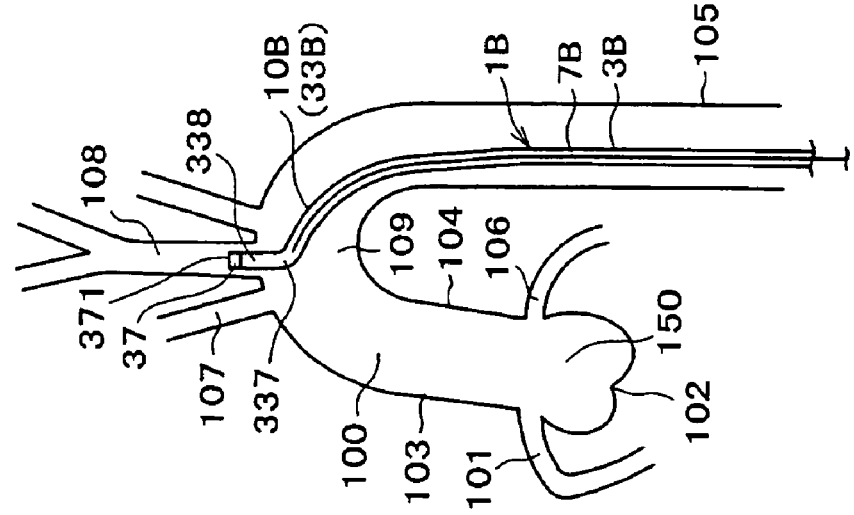
Figure 15C:
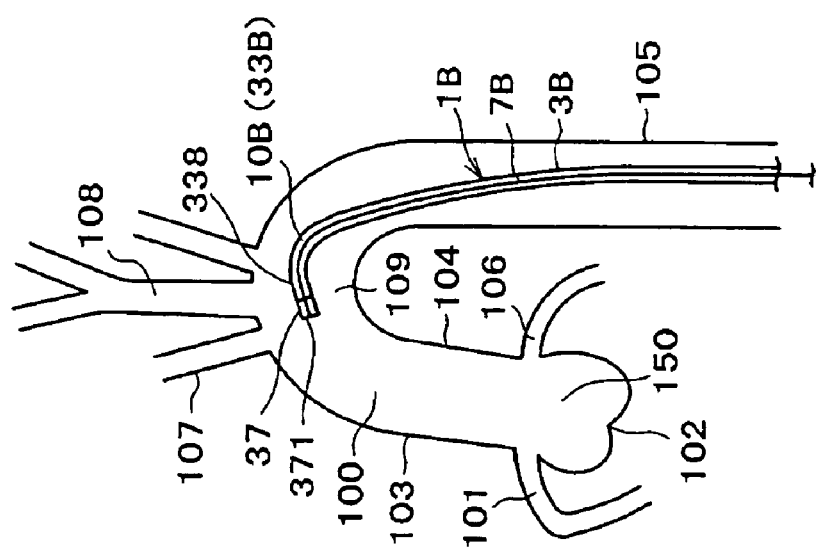

FIG. 12 is a partly omitted plan view showing the overall shape of a catheter assembly according to a further embodiment of the present invention. FIG. 13 is a partly omitted plan view showing the overall shape of an outer catheter constituting the catheter assembly according to the further embodiment of the present invention. FIG. 14 is a partly omitted plan view showing the overall shape of an inner catheter constituting the catheter assembly according to the further embodiment of the present invention. FIGS. 15A to 15C schematically illustrate a method of using the catheter assembly according to the present invention. FIGS. 16A to 16C schematically illustrate a method of using the catheter assembly according to the present invention. Herein, the right side in FIG. 12 (and in FIGS. 13 and 14 also) will be referred to as "the proximal end", the left side as "the distal end", the side closer to the proximal end as "proximal", and the side farther from the proximal end as "distal".

Now, a third embodiment of the catheter assembly according to the present invention will be described below referring to these figures, the description being centered on the differences from the above-described first embodiment. The same points as in the first embodiment should be understood by referring to the above description, and, therefore, description of these points will be omitted.

As shown in FIG. 12, the catheter assembly 1B according to the present invention comprises an outer catheter 2B, and an inner catheter 6B.

First, the outer catheter 2B will be described. The outer catheter 2B is composed of an outer catheter main body 3B, and a hub 4 attached (fixed) to the proximal end of the outer catheter main body 3B.

As shown in FIG. 13, the outer catheter main body 3B comprises a proximal portion 31 and an intermediate portion 32 which extend substantially rectilinearly, and a distal end portion 33B extending further from the intermediate portion 32 toward the distal end, in this order from the proximal end side. Besides, the distal end portion 33B is curved in a roughly S shape, in the condition where no external force is exerted thereon, in the same manner as above.

The distal end portion 33B comprises a first curved portion 333, a first distal portion 334, a second curved portion 335, a second distal portion 336, a third curved portion 337, and a distal end portion 338.

The first curved portion 333 is curved (bent) in shape at a predetermined angle relative to the intermediate portion 32. The angle (the angle formed between the intermediate portion 32 and the first distal portion 334) θ3 of the first curved portion 333 is not particularly limited, and is in the range of 60 to 120°, preferably 80 to 100°, and more preferably roughly rectangular. In addition, the radius of curvature of the center line of the first curved portion 333 is not particularly limited, and is preferably in the range of about 1 to 20 mm, more preferably about 4 to 10 mm.

The first distal portion 334 extends substantially rectilinearly from the first curved portion 333. The length of the first distal portion 334 is not particularly limited, and is preferably in the range of about 10 to 50 mm, more preferably about 20 to 40 mm.

The second curved portion 335 is curved in the direction opposite to the first curved portion 333 with respect to the first distal portion 334. The angle (the angle formed between the first distal portion 334 and the second distal portion 336) θ4 of the second curved portion 335 is not particularly limited, and is in the range of 60 to 120°, preferably 80 to 100°, and more preferably roughly rectangular. Besides, the radius of curvature of the center line of the second curved portion 335 is not particularly limited, and is preferably in the range of about 1 to 20 mm, more preferably about 4 to 10 mm.

The second distal portion 336 extends from the second curved portion 335 roughly rectilinearly or in a gradually curved shape. The length of the second distal portion 336 is not particularly limited, and is preferably in the range of about 10 to 80 mm, more preferably about 30 to 60 mm.

The third curved portion 337 is curved in shape in the same direction as the second curved portion 335. The angle (the angle formed between the second distal portion 336 and the distal end portion 338) θ5 of the third curved portion 337 is not particularly limited, and is in the range of 100 to 170°, preferably 120 to 150°. The radius of curvature of the center line of the third curved portion 337 is not particularly limited, and is preferably in the range of about 1 to 20 mm, more preferably about 5 to 15 mm.

The distal end portion 338 extends roughly rectilinearly from the third curved portion 337. The length of the distal end portion 338 is not particularly limited, and is preferably in the range of about 1 to 10 mm, more preferably about 2 to 6 mm.

The above-mentioned shape of the distal end portion 33B is such a shape as to enhance the position holding performance when the distal end portion 33B is held (made to indwell) in the left common carotid artery 108 or the right common carotid artery 112. Specifically, the first curved portion 333 ensures that the first distal portion 334 extending in the direction bent from the intermediate portion 32 of the outer catheter main body 3B conforms to the curve of the aortic arch 109, and the second curved portion 335 curved in the direction opposite to the first curved portion 333 ensures that the second distal portion 336 is directed toward the inlet of the left common carotid artery 108 located at the inside wall surface of the aortic arch 109 or toward the inlet of the brachiscephalic trunk 107 continuous with the right common carotid artery 112. Next, the third curved portion 337 in the same direction as the second curved portion 335 conforms to the blood vessel branch portion located next to the inlet, whereby the distal end portion 338 is directed toward the objective direction. Thus, each curved portion is designed to conform to each branch portion in the blood vessels, so that the distal end portion 33B can be provided with a strong backup force.

Next, the inner catheter 6B will be described. The inner catheter 6B is composed of an inner catheter main body 7B, and a hub 8 attached (fixed) to the proximal end of the outer catheter main body 3B.

As shown in FIG. 14, the inner catheter main body 7B comprises a proximal portion 71 and an intermediate portion 72 which extend substantially rectilinearly, and a distal end portion 73B extending from the intermediate portion 72 further toward the distal end and assuming a desired curved shape, in this order from the proximal end side. Besides, the curved shape is curved in a desired manner, in the condition where no external force is exerted, in the same manner as above.

The distal end portion 73B comprises a curved portion 735 and a distal end portion 736.

The curved portion 735 is curved (bent) at a predetermined angle (only in the same direction) relative to the intermediate portion 72, and assumes such a shape as not to intersect the intermediate portion 72. The angle (the angle formed between the intermediate portion 72 and the distal end portion 736) θ6 of the curved portion 735 is not particularly limited, and is in the range of 100 to 170°, preferably 120 to 150°. Besides, the radius of curvature of the center line of the third curved portion 337 is not particularly limited, and is preferably in the range of about 10 to 100 mm, more preferably about 30 to 70 mm.

The distal end portion 736 extends substantially rectilinearly from the curved portion 735. The length of the distal end portion 736 is not particularly limited, and is preferably in the range of 1 to 10 mm, more preferably about 2 to 6 mm.

Though not shown, the catheter assembly 1B is used after the guide wire 13 is inserted in the catheter assembly 1B in the assembled condition, in the same manner as above-mentioned. The shape of the catheter assembly 1B in the assembled condition in this instance is substantially rectilinear.

Next, one example of the method of using the catheter assembly 1B according to the present invention will be described.

Here, in the same manner as in the above-described first embodiment, the operations (maneuver) at the time of inserting the distal end 30 portion 10B of the catheter assembly 1B in the assembled condition into the left common carotid artery 108 and the right common carotid artery 112 respectively will be described in detail, based on FIGS. 15A to 15C and FIGS. 16A to 16C.

1. Insertion into Left Common Carotid Artery 108

In the same manner as in the above-described first embodiment, the distal end portion 10B of the catheter assembly 1B in the assembled condition is advanced through the abdominal aorta 105 to the inlet of the left common carotid artery 108 while causing the guide wire 13 to proceed. Thereafter, the guide wire 13 is withdrawn, to permit the shape of the distal end portion 10B to return to the original shape (the natural condition) of the catheter assembly 1B, as shown in FIG. 15A and FIG. 12.

Next, as shown in FIG. 15B, the distal end of the inner catheter 6B is pulled out to the third curved portion 337 of the outer catheter 2B, then, while confirming the position of the distal end of the distal end portion 10B (the distal end portion 338), the catheter assembly 1B in the assembled condition is pushed forwards to the inlet of the left common carotid artery 108, and the distal end portion 10B (the distal end portion 338) is inserted into the inlet. In this instance, since the distal end of the distal end portion 10B (the distal end portion 338) is directed toward the inlet of the left common carotid artery 108, the distal end portion 10B (the distal end portion 338) can be easily inserted into the inlet.

Furthermore, as shown in FIG. 15C, the distal end portion 10B (the distal end portion 33B) is pushed forward into the left common carotid artery 108 while withdrawing the inner catheter 6B from the catheter assembly 1B in the assembled condition. In this case, the catheter assembly 1B in the assembled condition is so operated that the distal end portion 10B (the distal end portion 33B) is directed toward the objective direction through the branch 108a of the left common carotid artery 108. Thereafter, the shape of the distal end portion 33B of the outer catheter 2B changes to the shape shown in FIG. 13, namely, to the shape suitable for backup, so that the distal end portion 33B is firmly fixed in the left common carotid artery 108.

Thereafter, though not shown, in the same manner as in the first embodiment, a distal end portion of a stent delivery catheter for carotid artery or the like is pushed forward to a constricted portion (stenosis portion) present in the left common carotid artery 108, and a dilation treatment using the stent is performed.

2. Insertion into Right Common Carotid Artery 112

In the same manner as in the above-described first embodiment, the distal end portion 10B of the catheter assembly 1B in the assembled condition is advanced through the abdominal aorta 105 to the inlet of the brachiocephalic trunk 107 while causing the guide wire 13 to proceed. Thereafter, the guide wire 13 is withdrawn, to permit the shape of the distal end portion 10B to return to the original curved shape (the natural condition) of the catheter assembly 1B, as shown in FIG. 16A and FIG. 12.

Next, as shown in FIG. 16B, the distal end of the inner catheter 6B is pulled out to the third curved portion 337 of the outer catheter 2B, then, while confirming the position of the distal end of the distal end portion 10B (the distal end portion 338), the catheter assembly 107 in the assembled condition is pushed forward to the inlet of the brachiocephalic trunk 107, and the distal end portion 10B (the distal end portion 338) is inserted into the inlet. In this instance, since the distal end of the distal end portion 10B (the distal end portion 338) is directed toward the inlet of the brachiocephalic trunk 107, the distal end portion 10B (the distal end portion 338) can be easily inserted into the inlet.

Further, as shown in FIG. 16C, while withdrawing the inner catheter 6B from the catheter assembly 1B in the assembled condition, the distal end portion 10B (the distal end portion 33B) is pushed forward (inserted) into the brachiocephalic trunk 107 and the right common carotid artery 112. In this case, the catheter assembly 1B in the assembled condition is so operated that the distal end portion 10B (the distal end portion 33B) is directed in the direction of the right common carotid artery 112 via the branch 107a of the brachiocephalic trunk 107. Thereafter, the shape of the distal end portion 33B of the outer catheter 2B changes to a shape suitable for backup, so that the distal end portion 33B is firmly fixed in the brachiocephalic trunk 107 and the right common carotid artery 112.

Thereafter, though not shown, in the same manner as in the first embodiment, a distal end portion of a stent delivery catheter for carotid artery or the like is pushed forward to a constricted portion (stenosis portion) present in the right common carotid artery 112, and a dilation treatment using a stent or the like is performed.

Thus, also in the catheter assembly 1B in the third embodiment, the distal end portion 10B (the distal end portion 33B) can be changed as required, in the same manner as in the above-described first embodiment.

The catheter assembly as above has a structure in which the shape of the distal end portion thereof is changed to a shape suitable for each site of the artery (for example, the left coronary artery, the right coronary artery, the left common carotid artery, the right common carotid artery, or the like).

The shapes of the distal end portion are a shape suitable for easy engagement with each site and a shape suitable for backup. By appropriate selection from these two shapes, easiness of engagement and assuredness of backup can be attained when needed, while using the single catheter assembly 1B. Namely, the easiness of engagement and the assuredness of backup can both be attained.

The present invention is not limited to the above-described embodiments, and each of the portions constituting the catheter assembly can be replaced with one of an arbitrary configuration which can display the same or similar function. Besides, arbitrary components may be added.

In addition, the catheter assembly according to the present invention may be a combination of arbitrary two or more configurations (characteristic features) selected from among the above embodiments.

As has been described above, according to the present invention, by using an outer catheter and an inner catheter different in distal end portion shape in combination, it is possible to attain both easiness of reaching to the site where the distal end portion is to be inserted and be made to indwell and enhancement of the force for fixation in the site.

Particularly, by selection between the condition where the inner catheter has been inserted in the outer catheter and the condition where the inner catheter has been withdrawn from the outer catheter, it is possible to change the distal end shape to the shape suitable for reaching to the site where the distal end portion is to be inserted and be made to indwell and to the shape suitable for a higher fixing force. Therefore, it is possible to attain both easy reaching and a higher fixing force.

In addition, where the distal end portion of the inner catheter is formed in a shape for easy reaching to the site where the distal end portion is to be inserted and be made to indwell whereas the distal end portion of the outer catheter is formed in a shape for enhancing the position holding performance, the above-mentioned effect is developed more conspicuously.

Besides, the catheter assembly according to the present invention does not damage the inside walls of blood vessels at the time of insertion into a living body, and is therefore highly safe.

What is claimed is:

1. A catheter assembly comprising an outer catheter having an outer catheter main body and an outer catheter hub attached to a proximal end of said outer catheter main body, and an inner catheter having an inner catheter main body insertable in said outer catheter main body and an inner catheter hub attached to a proximal end of said inner catheter main body, wherein a distal end portion of said outer catheter main body and a distal end portion of said inner catheter main body have different curved shapes, said distal end portion of said outer catheter main body is more flexible than said distal end portion of said inner catheter main body, said curved shape of said distal end portion of said outer catheter main body is deformed according to said curved shape of said distal end portion of said inner catheter main body when said inner catheter main body is inserted in said outer catheter main body so that their distal end portions overlap each other, the inner catheter hub includes at a distal end thereof an engaging portion for engagement with a proximal end of the outer catheter hub, and said outer catheter and said inner catheter are assembled when said inner catheter hub and said outer catheter hub are engaged with each other, and wherein said outer catheter hub and said inner catheter hub are respectively provided with engaging mechanisms, said inner and outer catheter hub being fixed to one another when the inner catheter is inserted into the outer catheter and the engaging mechanism of the outer catheter hub engages the engaging mechanism of the inner catheter hub, when said inner catheter is inserted into said outer catheter and said inner catheter hub is fixed to said outer catheter hub by the engaging mechanisms, the distal end portion of said outer catheter and the distal end portion of said inner catheter come to overlap each other and a distal end portion of the catheter assembly in the assembled condition is formed into a shape like the shape of said distal end portion of the inner catheter; wherein a distal end of said outer catheter and a distal end of said inner catheter coincide with each other when said outer catheter and said inner catheter are assembled.

2. A catheter assembly as set forth in claim 1, wherein said curved shape of said distal end portion of said outer catheter main body assumes a shape having a position maintaining property when said distal end portion is maintained in a target site where said distal end portion is to be inserted and be made to indwell.

3. A catheter assembly as set forth in claim 1, wherein said curved shape of said distal end portion of said outer catheter main body, in the condition where said inner catheter main body is inserted in said outer catheter main body so that the distal end portion of said outer catheter main body and the distal end portion of said inner catheter main body coincide substantially with each other, is the same as or substantially the same as said curved shape of said distal end portion of said inner catheter main body.

4. A catheter assembly as set forth in claim 1, wherein said curved shape of said distal end portion of said inner catheter main body comprises such a shape as to permit said catheter assembly to smoothly reach a target site where said distal end portion is to be inserted and be made to indwell.

5. A catheter assembly as set forth in claim 1, wherein said curved shape of said distal end portion of said outer catheter main body returns substantially to the original curved shape upon the transition from the condition where said inner catheter main body is inserted in said outer catheter main body to the condition where at least said distal end portion of said inner catheter main body is withdrawn from said distal end portion of said outer catheter main body.

6. A catheter assembly as set forth in claim 1, wherein the average of the radius of curvature of said distal end portion of said outer catheter is in the range of 25 to 60 mm.

7. A catheter assembly as set forth in claim 1, wherein the average of the radius of curvature of said distal end portion of said inner catheter is in the range of 5 to 25 mm.

8. A catheter assembly as set forth in claim 1, wherein said outer catheter main body is comprised of a laminate portion comprising at least three layers of an inner layer, an outer layer, and a reinforcement layer located therebetween, and a soft tip rich in flexibility provided on the distal end side of said laminate portion.

9. A catheter assembly as set forth in claim 8, wherein at least a part of said inner layer is comprised of a low-friction material.

10. A catheter assembly as set forth in claim 1, wherein said inner catheter is provided at said distal end portion thereof with a soft tip which is rich in flexibility.

11. A catheter assembly as set forth in claim 1, wherein said curved shape of said distal end portion of said outer catheter is such that said distal end portion is curved only in the same direction and has a loop for intersecting itself at least once.

12. A catheter assembly as set forth in claim 1, wherein said curved shape of said distal end portion of said outer catheter is such that said distal end portion has an S-shaped portion comprised of three curved portions and roughly rectilinear portions for connection between said curved portions and the distal end of said outer catheter main body.

13. A catheter assembly as set forth in claim 1, wherein said curved shape of said distal end portion of said inner catheter, prior to said inner catheter being inserted into said outer catheter, is such that said distal end portion of said inner catheter is curved only in the same direction and does not intersect itself.

14. A catheter assembly as set forth in claim 1, wherein bending stress on said distal end portion of said outer catheter main body in water at a temperature of 37 degrees C. is $\sigma 1$ [gf] and bending stress on said distal end portion of said inner catheter main body in water at a temperature of 37 degrees C. is $\sigma 2$ [gf], and the ratio $\sigma 2/\sigma 1$ is in the range of from 1.05 to 3.

15. A catheter assembly as set forth in claim 14, wherein said bending stress $\sigma 1$ is in the range of from 10 to 400 gf.

16. A catheter assembly as set forth in claim 14, wherein said bending stress $\sigma 2$ is in the range of from 20 to 500 gf.

17. A method of disposing a catheter in a cardiac blood vessel, said method comprising the steps of:
   providing an outer catheter which comprises an outer catheter main body comprising a distal end curved portion having a first curved shape and a position maintaining property and an outer catheter hub attached to a proximal end of said outer catheter main body;
   providing an inner catheter which comprises an inner catheter main body comprising a distal end curved portion having a second curved shape different from said first curved shape and an inner catheter hub attached to a proximal end of said inner catheter main body;
   preparing a catheter assembly having a distal end curved portion different from said first curved shape, which comprises inserting said inner catheter main body into the proximal end of said outer catheter hub until said outer catheter hub and said inner catheter hub are engaged with each other, so that said distal end of said outer catheter and said distal end of said inner catheter coincide with one another and the distal end portion of said outer catheter and the distal end portion of said inner catheter come to overlap each other and a distal end portion of the catheter assembly in the assembled condition is formed into a shape like the shape of said distal end portion of the inner catheter;
   disposing the distal end of said catheter assembly at a coronary artery port in an aorta;
   withdrawing said inner catheter from said catheter assembly with said distal end thereof disposed at the coronary artery port, to thereby develop said first curved shape of said distal end curved portion of said outer catheter which possesses the position maintaining property; and
   introducing a contrast medium into the coronary artery port by way of the outer catheter after withdrawing said inner catheter from said outer catheter in the proximal direction of said outer catheter.

18. A method of disposing a catheter in a cardiac blood vessel comprising:
   providing an outer catheter which comprises an outer catheter main body comprising a distal end curved portion having a first curved shape and a position maintaining property and an outer catheter hub attached to a proximal end of said outer catheter main body;
   providing an inner catheter which comprises an inner catheter main body comprising a distal end curved portion having a second curved shape different from said first curved shape and an inner catheter hub attached to a proximal end of said inner catheter main body;
   preparing a catheter assembly by inserting said inner catheter main body into the proximal end of said outer catheter hub until said outer catheter hub and said inner catheter hub are engaged with each other, with said distal end of said outer catheter and said distal end of said inner catheter overlapping each other to produce a distal end curved portion of the catheter assembly that is different from said first curved shape;
   disposing a distal end of said catheter assembly at a coronary artery port in an aorta;
   withdrawing said inner catheter from said outer catheter in a proximal direction of the outer catheter while the distal end of the catheter assembly is disposed at the coronary artery port to develop said first curved shape of said distal end curved portion of said outer catheter which possesses the position maintaining property; and
   introducing a contrast medium into the coronary artery port by way of the outer catheter after withdrawing said inner catheter from said outer catheter in the proximal direction of said outer catheter.

19. A method of disposing a catheter in a cardiac blood vessel comprising:
   providing an outer catheter which comprises an outer catheter main body comprising a distal end curved portion having a first curved shape and a position maintaining property and an outer catheter hub attached to a proximal end of said outer catheter main body;
   providing an inner catheter which comprises an inner catheter main body comprising a distal end curved portion having a second curved shape different from said first curved shape and an inner catheter hub attached to a proximal end of said inner catheter main body;

preparing a catheter assembly by inserting said inner catheter main body into the proximal end of said outer catheter hub until said outer catheter hub and said inner catheter hub are engaged with each other, with said distal end of said outer catheter and said distal end of said inner catheter overlapping each other to produce a distal end curved portion of the catheter assembly that is different from said first curved shape;

disposing a distal end of said catheter assembly at a coronary artery port in an aorta;

withdrawing said inner catheter from said outer catheter in a proximal direction of the outer catheter while the distal end of the catheter assembly is disposed at the coronary artery port to develop said first curved shape of said distal end curved portion of said outer catheter which possesses the position maintaining property; and introducing a procedure catheter into the coronary artery port by way of the outer catheter after withdrawing said inner catheter from said outer catheter in the proximal direction of said outer catheter;

and introducing a contrast medium into the coronary artery port by way of the outer catheter after withdrawing said inner catheter from said outer catheter in the proximal direction of said outer catheter.

20. A method according to claim 19, wherein the procedure catheter introduced into the coronary artery port is a balloon catheter.

* * * * *